(12) United States Patent
Maeda et al.

(10) Patent No.: US 7,985,197 B2
(45) Date of Patent: Jul. 26, 2011

(54) THERAPEUTIC-SUBSTANCE CARRYING/ADMINISTERING APPLIANCE

(75) Inventors: Masanori Maeda, Tokyo (JP); Hidenori Takushima, Saitama (JP); Teruo Okano, Chiba (JP); Masayuki Yamato, Tokyo (JP); Hiroshi Iseki, Tokyo (JP); Ryoichi Nakamura, Kanagawa (JP); Takamasa Onuki, Kanagawa (JP); Masato Kanzaki, Tokyo (JP); Takashi Suzuki, Tokyo (JP); Shigeru Nagai, Kanagawa (JP)

(73) Assignees: Hoya Corporation, Tokyo (JP); Tokyo Women's Medical University, Tokyo (JP)

( * ) Notice: Subject to any disclaimer, the term of this patent is extended or adjusted under 35 U.S.C. 154(b) by 64 days.

(21) Appl. No.: 12/123,005

(22) Filed: May 19, 2008

(65) Prior Publication Data
US 2008/0294093 A1 Nov. 27, 2008

(30) Foreign Application Priority Data

May 22, 2007 (JP) .................................. 2007-135848
May 9, 2008 (JP) .................................. 2008-122814

(51) Int. Cl.
*A61M 31/00* (2006.01)

(52) U.S. Cl. ........................................................ 604/60

(58) Field of Classification Search ................ 604/60, 604/13; 606/151; 600/37
See application file for complete search history.

(56) References Cited

U.S. PATENT DOCUMENTS

| | | | | |
|---|---|---|---|---|
| 4,836,201 A | * | 6/1989 | Patton et al. | ................... 606/107 |
| 4,880,000 A | * | 11/1989 | Holmes et al. | ................ 606/107 |
| 5,310,650 A | | 5/1994 | McMahon et al. | |
| 5,370,650 A | * | 12/1994 | Tovey et al. | ................... 606/151 |
| 5,405,360 A | | 4/1995 | Tovey | |
| 5,503,623 A | | 4/1996 | Tilton, Jr. | |
| 6,193,731 B1 | | 2/2001 | Oppelt et al. | |
| 7,048,710 B1 | * | 5/2006 | Cragg et al. | .................... 604/15 |
| 7,063,681 B1 | * | 6/2006 | Peery | ............................... 604/60 |
| 2007/0049950 A1 | | 3/2007 | Theroux et al. | |

(Continued)

FOREIGN PATENT DOCUMENTS

JP 2007-10452 1/2007

(Continued)

OTHER PUBLICATIONS

English language Abstract of JP 2007-10452, Jan. 18, 2007.

(Continued)

*Primary Examiner* — Nicholas D Lucchesi
*Assistant Examiner* — Brooke M Matney
(74) *Attorney, Agent, or Firm* — Greenblum & Bernstein P.L.C.

(57) ABSTRACT

A therapeutic-substance carrying/administering appliance includes a cylindrical outer sheath; a slide member installed in the cylindrical outer sheath to be slidable therein; and a sheet supporting member, connected to a distal end of the slide member and made of a resilient material, for supporting a sheet-shaped therapeutic substance. The sheet supporting member is held in a flat unrolled shape in a free state in which the sheet supporting member projects outwardly from a distal end of the cylindrical outer sheath. When the sheet supporting member is in the free state, sliding the slide member in a retracting direction causes the sheet supporting member to contact the distal end of the cylindrical outer sheath, and subsequently further moving the slide member in the retracting direction causes the sheet supporting member to be retracted into the cylindrical outer sheath while being deformed into a tubular shape.

14 Claims, 20 Drawing Sheets

U.S. PATENT DOCUMENTS

| | | |
|---|---|---|
| 2007/0073247 A1 | 3/2007 | Ewaschuk |
| 2007/0078483 A1 | 4/2007 | Ewaschuk et al. |
| 2007/0088351 A1 | 4/2007 | Ewaschuk et al. |
| 2007/0185504 A1 | 8/2007 | Manetakis et al. |
| 2007/0208422 A1 | 9/2007 | Walter et al. |

FOREIGN PATENT DOCUMENTS

| | | | |
|---|---|---|---|
| WO | WO 2007027592 A1 | * | 3/2007 |

OTHER PUBLICATIONS

Dynamic Sealing of Lung Air Leaks by the Transplantation of Tissue Engineered Cell Sheets', in the Biomaterials 28 (2007) 4294-4302, URL: http://www.elsevier.com/locate/biomaterials, Jun. 28, 2007.

Kanzaki, "Attempt to close intraoperative air leakage with cell sheet", in the abstract journal of the third congress of the Japanese Society for Regenerative Medicine in 2003.

* cited by examiner

THERAPEUTIC-SUBSTANCE CARRYING/ADMINISTERING APPLIANCE

BACKGROUND OF THE INVENTION

1. Field of the Invention

The present invention relates to a medical appliance for carrying a sheet-shaped therapeutic substance to an affected site and administering the same to the affected site.

2. Description of the Prior Art

In surgical operations for respiratory organ illnesses, a treatment in which a sheet-shaped (cloth-like) substance made of a biodegradable/bioabsorbable material such as polyglycolic acid is stuck to an organ to reinforce sutures or to prevent air from leaking from the sutures is often performed. Additionally, as shown in a non-patent publication entitled "ATTEMPT TO STOP INTRAOPERATIVE AIR LEAK BY A CELL SHEET" in the abstract journal of the third congress of the Japanese Society for Regenerative Medicine in 2003, and in a non-patent publication entitled "DYNAMIC SEALING OF LUNG AIR LEAKS BY THE TRANSPLANTATION OF TISSUE ENGINEERED CELL SHEETS" in the Biomaterials 28 (2007) 4294-4302, available online (http://www.elsevier.com/locate/biomaterials) from Jun. 28, 2007, a treatment technique in which autologous cells are cultured to be regenerated into a cell sheet which is transplanted onto an affected site has been proposed. In recent years, endoscopic operations have been widely carried out as minimally invasive operations, and endoscopic forceps have mainly been used for carrying and administering a therapeutic substance such as the aforementioned sheet-shaped substance.

However, to bring a sheet-shaped therapeutic substance, which is liable to be damaged and tends to stick to itself, to an affected site and then spread the sheet-shaped therapeutic substance in order to transplant the sheet-shaped therapeutic substance precisely to an affected site with the use of a forceps, an advanced technique is required and making an improvement to the workability of the transplanting has been desired. Under these circumstances, the assignee of the present patent application has proposed a medical appliance for carrying a sheet-shaped therapeutic substance to an affected site and administering the medical appliance to the affected site, which is disclosed in Japanese patent application No. 2007-10452. This medical appliance can make a resiliently deformable sheet supporting element thereof that supports a sheet-shaped therapeutic substance deformed between a flat unrolled shape and a tubular housed shape, and can also make a proximal end of the sheet supporting element perform a bending operation by variations in fluid pressure of a fluid supplied in the medical appliance.

Structurally, the therapeutic-substance carrying/administering appliance disclosed in the aforementioned Japanese patent application needs to be provided with minute fluid channels inside the sheet supporting element thereof, and the circulation of the fluid filled in the minute fluid channels needs to be strictly controlled, and accordingly, there is room to improve the production cost and the reliability of the appliance when it is in operation.

SUMMARY OF THE INVENTION

The present invention provides a therapeutic-substance carrying/administering appliance which can be obtained at a lower cost of production than before, excels in reliability and can administer a sheet-shaped therapeutic substance to an affected site easily and securely.

According to an aspect of the present invention, a therapeutic-substance carrying/administering appliance is provided, including a cylindrical outer sheath; a slide member installed in the cylindrical outer sheath to be slidable in an axial direction; and a sheet supporting member, connected to a distal end of the slide member and made of a resilient material, for supporting a sheet-shaped therapeutic substance. The sheet supporting member is held in a flat unrolled shape in a free state in which the sheet supporting member projects outwardly from a distal end of the cylindrical outer sheath. When the sheet supporting member is in the free state, sliding the slide member in a retracting direction into the cylindrical outer sheath causes the sheet supporting member to come in contact with the distal end of the cylindrical outer sheath, and subsequently further moving the slide member in the retracting direction causes the sheet supporting member to be retracted into the cylindrical outer sheath while being deformed into a tubular shape.

It is desirable for the sheet supporting member to include a sheet-supporting sheet portion which supports the sheet-shaped therapeutic substance, a connecting portion connected to the distal end of the slide member, and a tapered portion positioned between the sheet-supporting sheet portion and the connecting portion and shaped so that a width thereof gradually reduces in a direction from the sheet-supporting sheet portion to the connecting portion. When the sheet supporting member is moved in the retracting direction from the free state, in which the sheet supporting member is held in the flat unrolled shape, the sheet supporting member is deformed into the tubular shape by sliding contact between the tapered portion and the distal end of the cylindrical outer sheath.

In this case, the sheet supporting member can be deformed more easily if the distal end of the cylindrical outer sheath includes a beveled surface inclined to a plane orthogonal to an axis of the cylindrical outer sheath.

It is desirable for the outer and inner edges of said beveled surface are chamfered.

It is desirable for the sheet supporting member to be connectable to and disconnectable from the distal end of the slide member in a radial direction of the cylindrical outer sheath, and for the therapeutic-substance carrying/administering appliance to include a movement limit device which limits a moving range of the slide member within a range in which an inner peripheral surface of the cylindrical outer sheath prevents the sheet supporting member from being disconnected from the distal end of the slide member.

It is desirable for the movement limit device to include a groove formed on the slide member, and a screw screwed into the cylindrical outer sheath to be engaged in the groove.

The sheet supporting member having a wider width can be accommodated in the outer sheath if the cylindrical outer sheath includes a partition wall positioned inside the cylindrical outer sheath to increase an inner peripheral area of the cylindrical outer sheath.

It is desirable for the partition wall to project radially inwards from the inner peripheral surface of the cylindrical outer sheath to a position so that internal spaces of the cylindrical outer sheath on opposite sides of the partition wall are communicatively connected to each other.

It is desirable for the therapeutic-substance carrying/administering appliance to include a connecting member positioned between the sheet supporting member and the slide member, wherein the sheet supporting member in the free state is supported by the connecting member to be flat and substantially parallel to an axis of the cylindrical outer sheath.

It is desirable for the therapeutic-substance carrying/administering appliance to include a connecting member positioned between the sheet supporting member and the slide member, wherein the sheet supporting member in the free state supported by the connecting member to be flat and inclined to an axis of the cylindrical outer sheath.

It is desirable for the sheet supporting member in the free state to include a portion shaped to be asymmetrical with respect to a central axis of the sheet supporting member, wherein the central axis is parallel to an axis of the cylindrical outer sheath and passes through a connecting portion of the sheet supporting member which is connected to the distal end of the slide member. Accordingly, the sheet supporting member can be retracted into the outer sheath smoothly while preventing the overlapping portions of the sheet supporting member from interfering with each other. More specifically, the sheet supporting member can be shaped so that the asymmetrical-shaped portion of the sheet supporting member is formed in a vicinity of the connecting portion or so that an entire part of the sheet supporting member, from opposite ends in a direction of the central axis, is shaped to be bilaterally asymmetrical with respect to the central axis.

In an embodiment, a therapeutic-substance carrying/administering appliance is provided, including a cylindrical outer sheath; a slide rod inserted in the cylindrical outer sheath to be slidable relative to the cylindrical outer sheath; and a resilient sheet fixed to a distal end of the slide rod, a sheet-shaped therapeutic substance being mountable on the resilient sheet. The resilient sheet is flat in a free state in which the resilient sheet projects outwardly from the distal end of the cylindrical outer sheath. Sliding the slide rod in a retracting direction into the cylindrical outer sheath causes laterally opposite edges of the resilient sheet in a vicinity of the distal end of the slide rod to slide on the distal end of the cylindrical outer sheath while the resilient sheet is deformed into a tubular shape to be retracted into the cylindrical outer sheath.

According to the therapeutic-substance carrying/administering appliance to which the present invention is applied, a sheet-shaped therapeutic substance can be brought to a transplantation site in a human body with a low degree of invasive medical procedure to the human body by deforming the sheet supporting member into a tubular shape and retracting this tubular sheet supporting member into the outer sheath. Additionally, by simply pushing the slide member in the projecting direction upon the sheet supporting member reaching the transplantation site, the sheet supporting member naturally unrolls due its shape-sustaining ability (resiliency), and accordingly, the sheet-shaped therapeutic substance can be transplanted very easily and reliably compared to a conventional method using a forceps or the like. Since this therapeutic-substance carrying/administering appliance according to the present invention has a simple structure with the flexible sheet supporting member that is deformed between an unrolled shape and a tubular shape in accordance with advancing/retracting movements of the slide member, there is little possibility of inconvenience such as a malfunction occurring; moreover, the cost of production can also be minimized.

The present disclosure relates to subject matter contained in Japanese Patent Applications Nos. 2007-135848 (filed on May 22, 2007) and 2008-122814 (filed on May 9, 2008) which are expressly incorporated herein by reference in their entireties.

BRIEF DESCRIPTION OF THE DRAWINGS

The present invention will be described below in detail with reference to the accompanying drawings in which.

DESCRIPTION OF THE PREFERRED EMBODIMENTS

Figure 1:
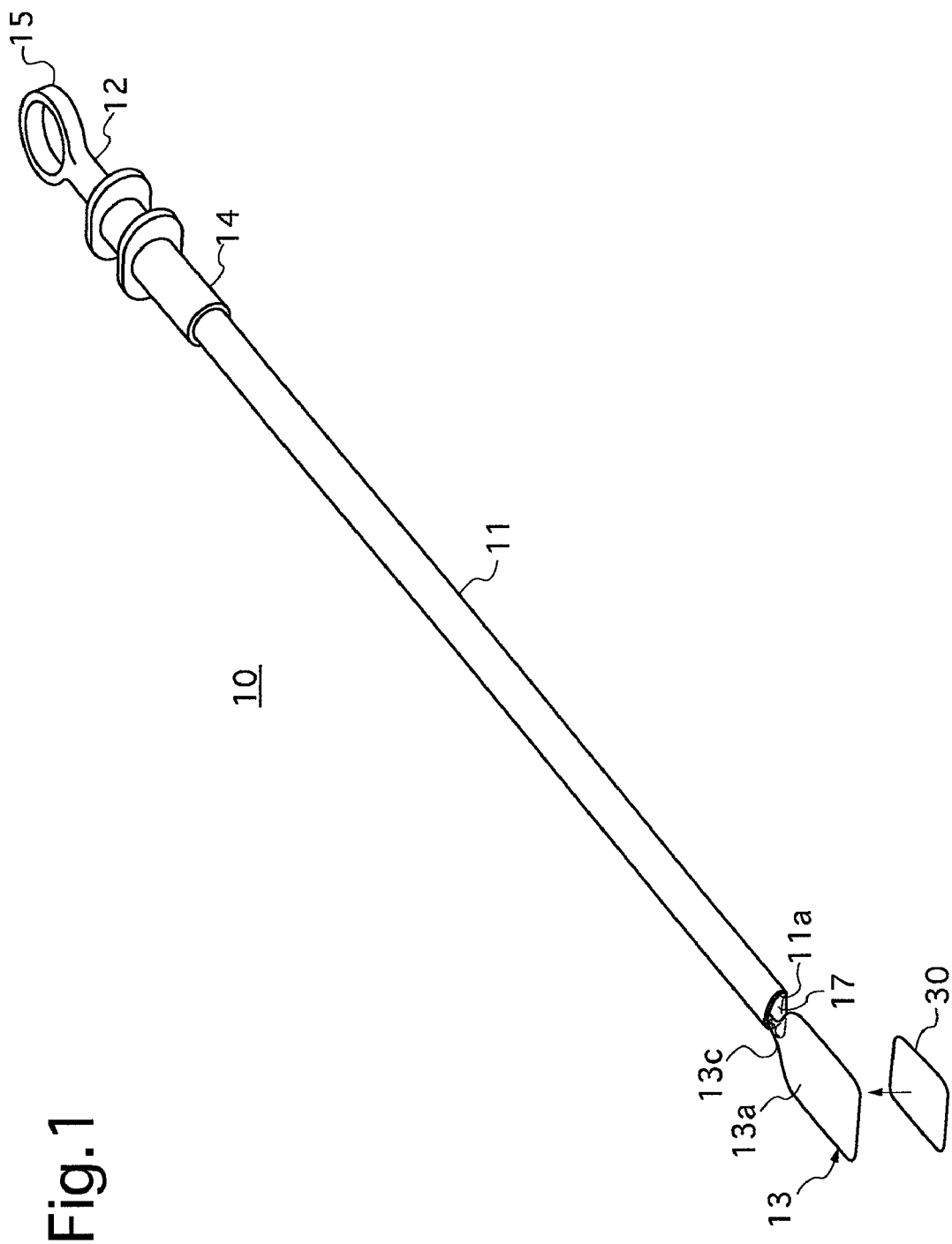
FIG. 1 is a perspective view of an embodiment of a therapeutic-substance carrying/administering appliance according to the present invention and a sheet-shaped therapeutic-substance which is to be carried by the therapeutic-substance carrying/administering appliance, showing a state where a sheet supporting element projects from the distal end of the outer sheath of the appliance and has fully expanded.

FIGS. 1 through 4 show the overall structure of an embodiment (first embodiment) of a therapeutic-substance carrying/administering appliance. The therapeutic-substance carrying/administering appliance 10 is provided with a hollow-cylindrical outer sheath 11, a slide member (slide rod) 12 and a sheet supporting element (sheet supporting member) 13. The slide member 12 is slidably fitted into the outer sheath 11 and supported thereby. The sheet supporting element 13 is fixed to the distal end (left end with respect to FIGS. 3 and 4) of the slide member 12. In the following descriptions, "axial direction" and "radial directions" designate the axial direction (lengthwise direction) and radial directions of the outer sheath 11, respectively. The outer sheath 11 is provided, at one end (proximal end) thereof in the axial direction, with a grip portion 14 having a pair of finger flanges 14a (see FIGS. 5 and 6) which are separate from each other in the axial direction. The slide member 12 is provided, at one end (proximal end) thereof which projects outwardly from the proximal end of the outer sheath 11, with a ring-shaped finger insertion portion 15. When the slide member 12 is manually slid relative to the outer sheath 11, the slide member 12 can be manually slid in an easy manner if the slide member 12 is slid by movements of thumb inserted in the finger insertion portion 15 with a portion of the outer sheath 11 between the pair of finger flanges 14a being held between forefinger and middle finger of the same hand. An end surface of the other end of the outer sheath 11 is formed as a beveled surface 11a lying in a plane inclined to a plane P (shown by one-dot chain lines in FIG. 8) orthogonal to the axis of the outer sheath 11. The angle of inclination of the beveled surface 11a is approximately 30 degrees. The outer and inner edges of the beveled surface 11a are chamfered to ensure a smooth end shape.

Figure 6:
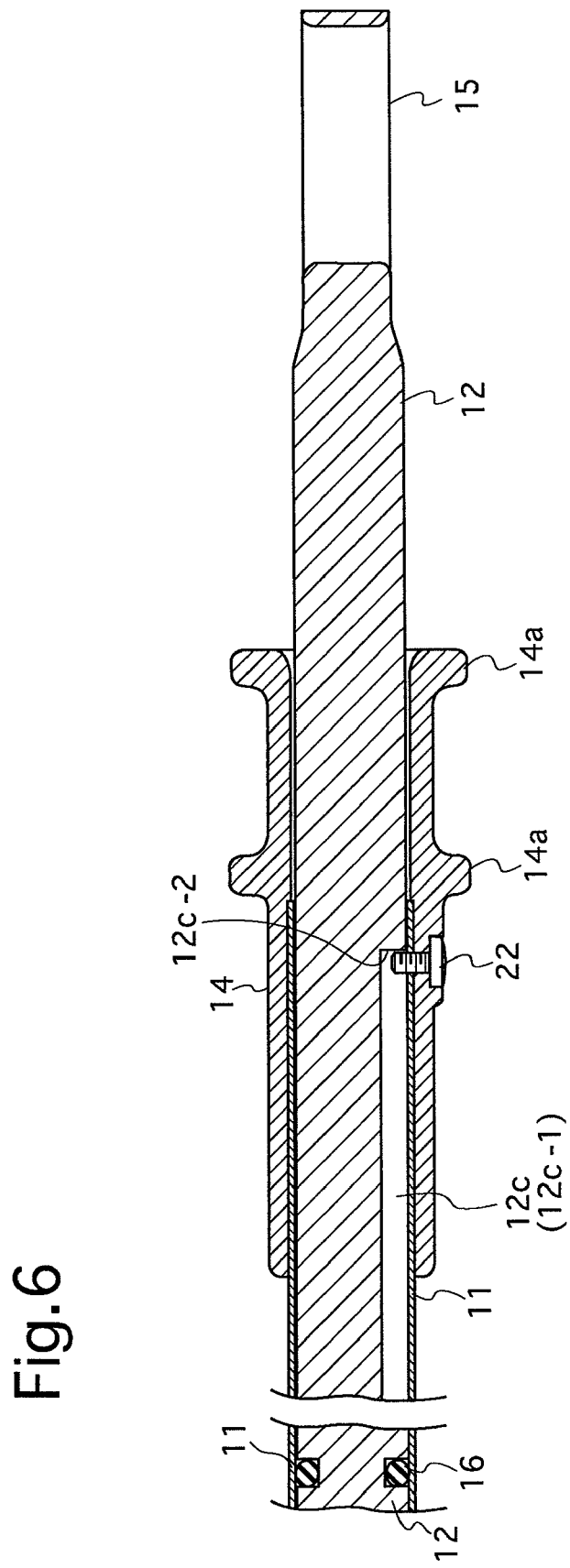
FIG. 6 is a longitudinal cross sectional view of a portion of the therapeutic-substance carrying/administering appliance in the vicinity of the hold/control portion thereof.

As shown in FIG. 6, the therapeutic-substance carrying/administering appliance 10 is provided between the inner peripheral surface of the outer sheath 11 and the slide member 12 with an O-ring 16. The O-ring 16 has the following capabilities: the capability of preventing air which may pass through the inside of the outer sheath 11 and come out therefrom into an exterior space from the interior of a body from leaking to the exterior space during use of the therapeutic-substance carrying/administering appliance 10, the capability of applying a moderate resistance to the sliding operation of the slide member 12, and the capability of preventing the slide member 12 from tilting relative to the outer sheath 11 (i.e., maintaining concentricity of the slide member 12 with the outer sheath 11). Although only one O-ring 16 is shown in FIG. 6, two or more O-rings 16 can be installed at different positions in the axial direction of the outer sheath 11. Additionally, one or more O-rings each of which being similar to the O-ring 16 can be installed between an outer peripheral surface of a connecting member 17 (which will be discussed in later) and an inner peripheral surface of the outer sheath 11.

Figure 7:
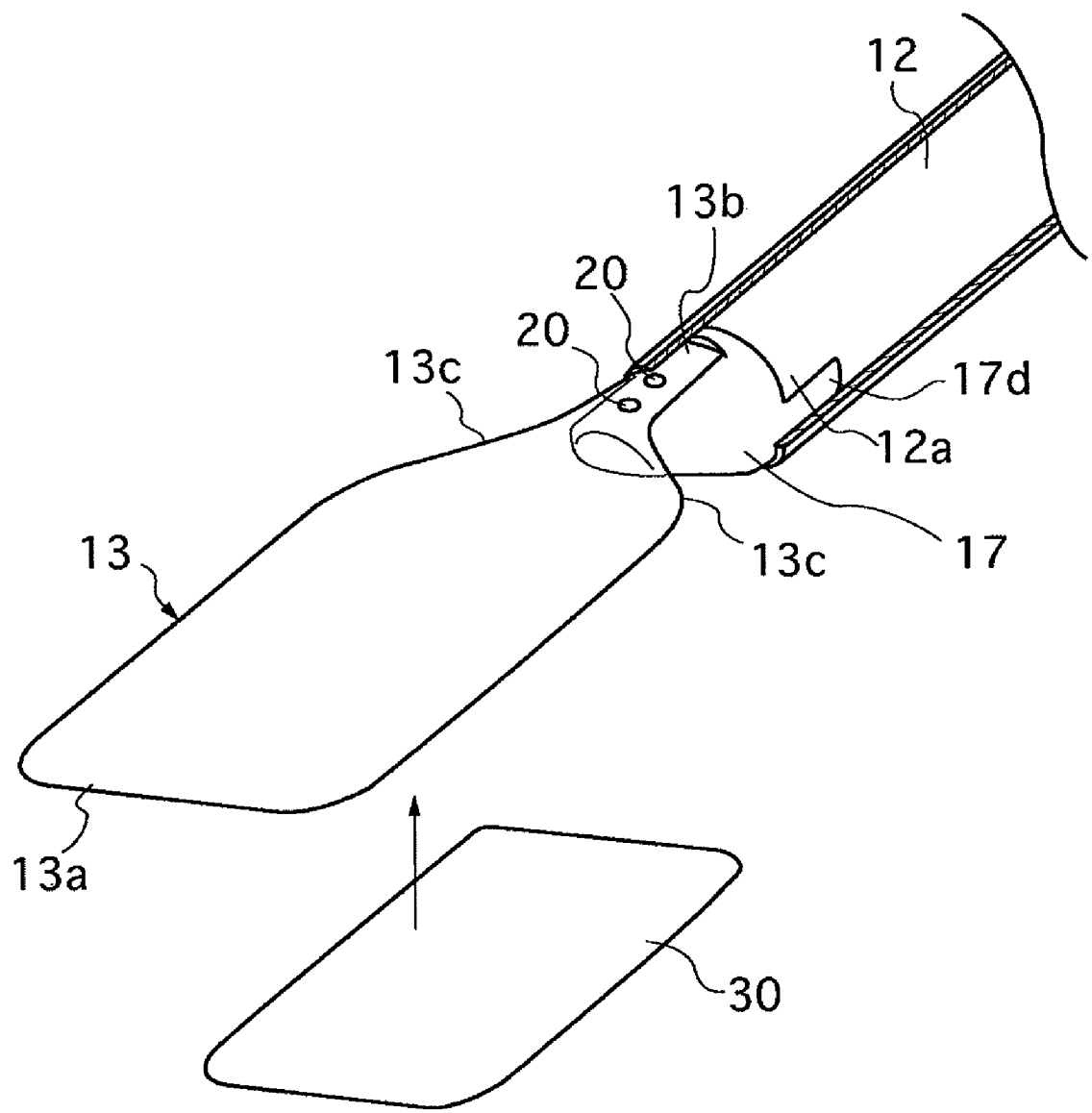
FIG. 7 is a perspective view, partly in cross section, of a portion of the therapeutic-substance carrying/administering appliance in the vicinity of the distal end of the outer sheath thereof in a state where the sheet supporting element projects outward from the distal end of the outer sheath and has fully expanded and a sheet-shaped therapeutic-substance which is to be carried by the therapeutic-substance carrying/administering appliance, showing a part of the outer sheath in cross section.
Figure 11:
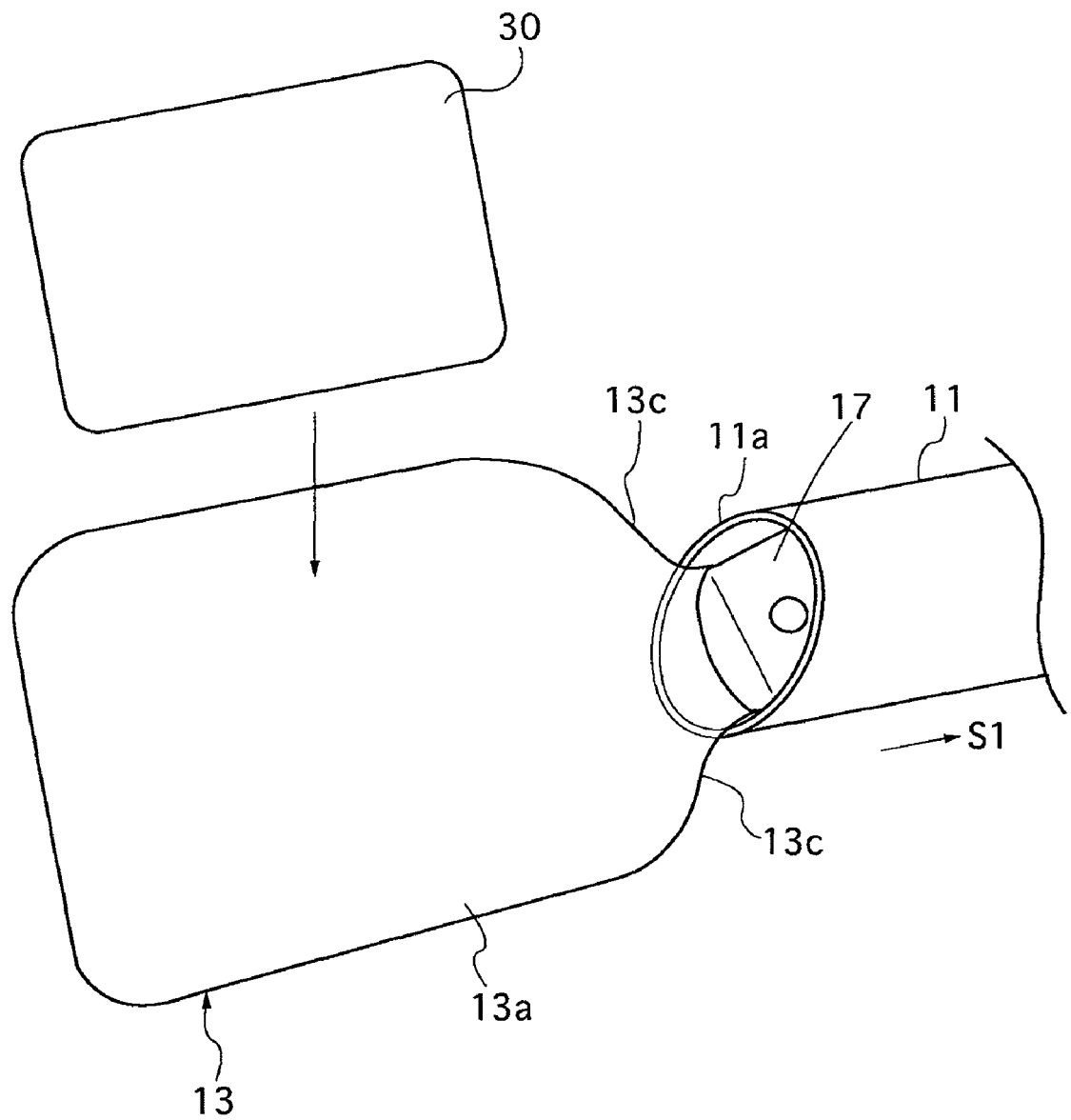
FIG. 11 is a perspective view of a portion of the therapeutic-substance carrying/administering appliance in the vicinity of the distal end of the outer sheath thereof and a sheet-shaped therapeutic-substance which is to be carried by the therapeutic-substance carrying/administering appliance, showing a state where the sheet supporting element projects from the distal end of the outer sheath and has fully expanded into a flat shape.

The sheet supporting element 13 is a flexible and resilient thin plate member and provided with a sheet-supporting sheet portion 13a, a connecting portion 13b, and a tapered portion 13c positioned between the sheet-supporting sheet portion 13a and the connecting portion 13b. The sheet-supporting sheet portion 13a is made to support a therapeutic substance 30 in the shape of a sheet (hereinafter referred to as a sheet 30) shown in FIGS. 1, 7 and 11. The connecting portion 13b is positioned at the base (fixed end) of the sheet supporting element 13. The tapered portion 13c is shaped so that the width thereof gradually reduces in the direction from the sheet-supporting sheet portion 13a to the connecting portion 13b. The tapered portion 13c has a pair of side edges which are substantially symmetrical with respect to the axis of the outer sheath 11. Each side edge of this pair of side edges is formed as a combination of a convex arc edge (edge having a predetermined radius of curvature) which is continuous with the sheet-supporting sheet portion 13a, and a concave arc edge (edge having a predetermined radius of curvature) which is continuous with the connecting portion 13b. The resiliency of the sheet supporting element 13 keeps the sheet-supporting sheet portion 13a in an unrolled flat shape as shown in FIGS. 7 and 11 when in a free state, i.e., in a state where no external force is exerted on the sheet supporting element 13.

Figure 8:
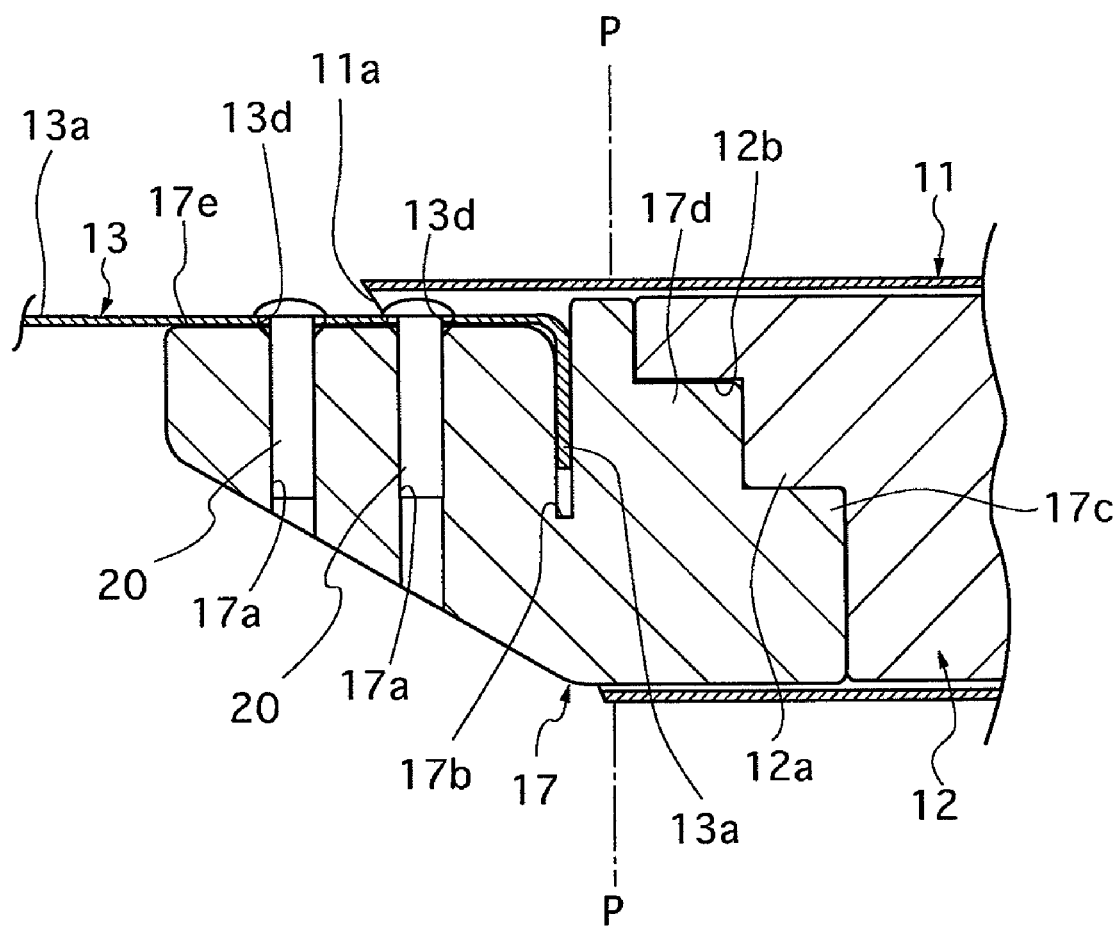
FIG. 8 is a longitudinal cross sectional view of a portion of the therapeutic-substance carrying/administering appliance in the vicinity of the junction between a slide member and a connecting member.
Figure 9:
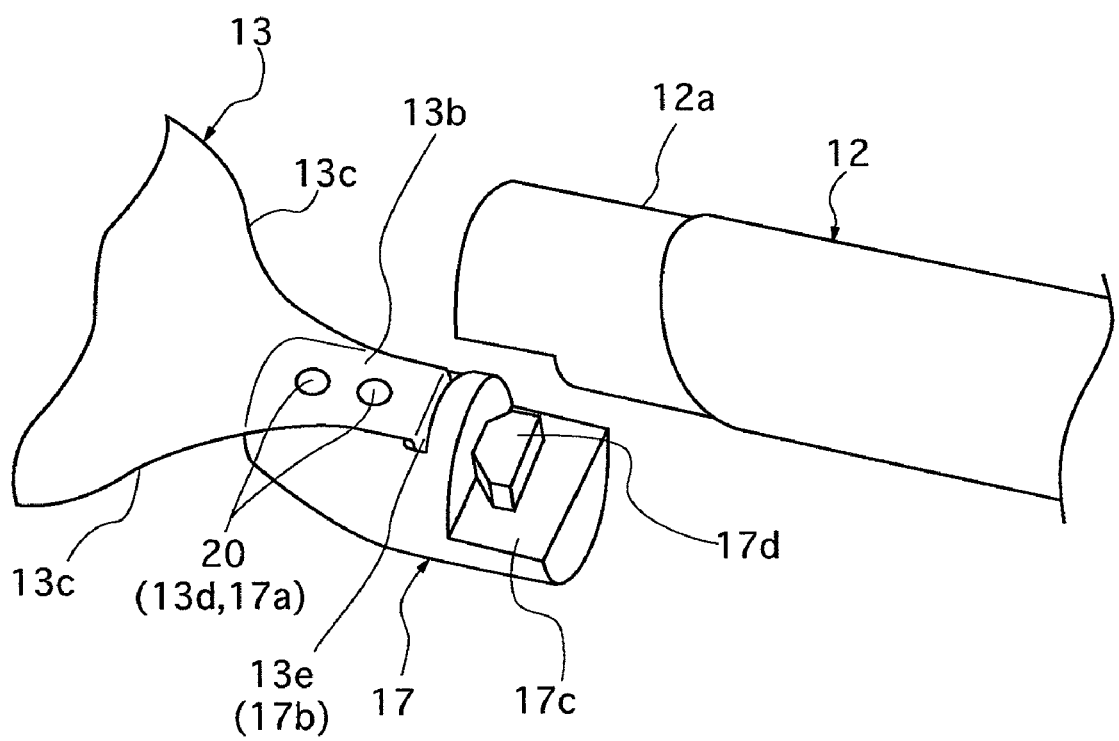
FIG. 9 is an exploded perspective view of a portion of the therapeutic-substance carrying/administering appliance in the vicinity of the distal end of the outer sheath thereof, showing a state where a combination of the sheet supporting element and the connecting member is removed from the distal end of the slide member.
Figure 10:
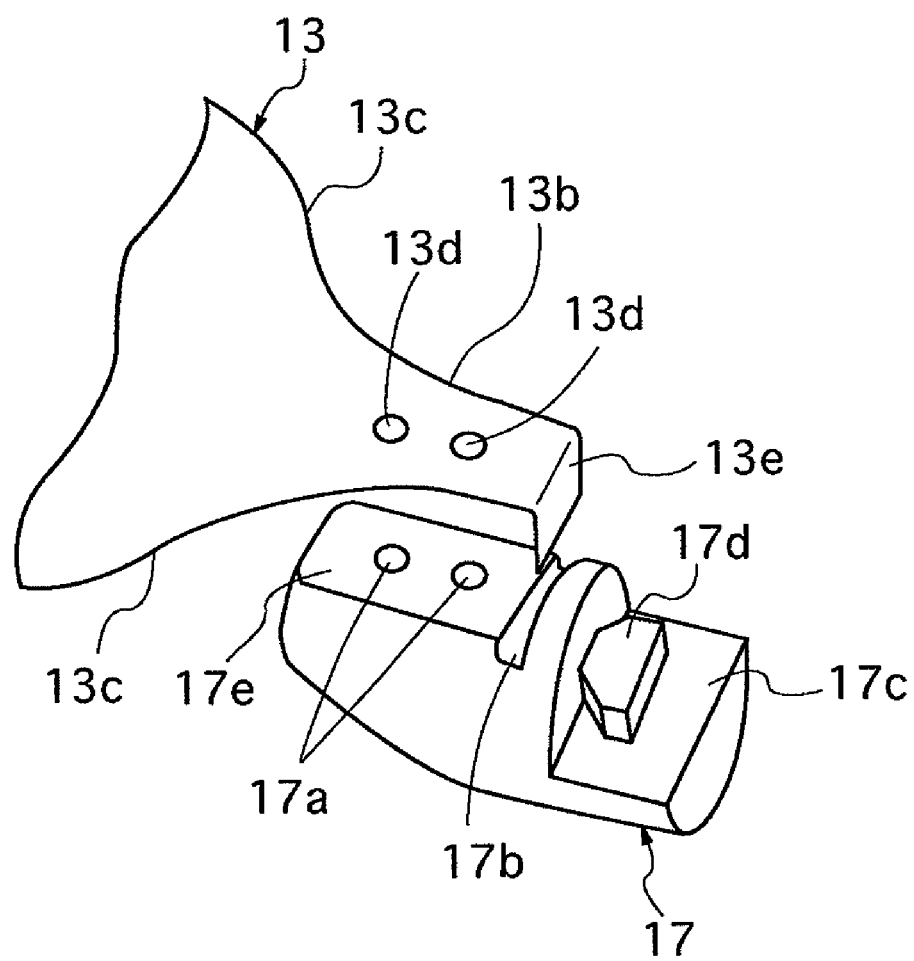
FIG. 10 is an exploded perspective view of the connecting member and the sheet supporting element.

The sheet supporting element 13 and the slide member 12 are connected to each other via a connecting member 17. As shown in FIGS. 8 through 10, the connecting member 17 is provided with two screw holes 17a, an insertion groove 17b and a stepped engaging portion 17c in that order from the front end side of the connecting member 17. The connecting member 17 is provided on the stepped engaging portion 17c with a disengaging movement preventive projection 17d. The connecting member 17 is provided, on a portion thereof in which the two screw holes 17a are formed, with a flat support surface 17e, substantially parallel to the axis of the outer sheath 11. The connecting portion 13b of the sheet supporting element 13 is provided with two through holes 13d which are positioned to correspond to the two screw holes 17a of the connecting member 17, respectively, and is further provided at the rear end of the connecting portion 13b with a bent end 13e engageable in the insertion groove 17b which is bent into a substantially right angle. If the connecting portion 13b is placed onto the flat support surface 17e with the bent end 13e being engaged in the insertion groove 17b, the two through holes 13d are aligned with the two screw holes 17a of the connecting member 17, respectively. The sheet supporting element 13 and the connecting member 17 are secured to each other by two set screws 20 which are screwed into the two screw holes 17a through the two through holes 13d, respectively. Alternatively, the sheet supporting element 13 and the connecting member 17 can be secured to each other by two securing pins which are press-fitted into the two screw holes 17a through the two through holes 13d, respectively.

The slide member 12 is provided with a stepped engaging portion 12a which is engaged with the stepped engaging portion 17c of the connecting member 17, and is provided on the stepped engaging portion 12a with a disengaging movement preventive recess (shown only in cross section in FIG. 8) 12b in which the disengaging movement preventive projection 17d of the connecting member 17 is engaged. As shown in FIG. 9, the disengaging movement preventive projection 17d that is provided on the connecting member 17 is a trapezoidal projection, the width of which increases in a direction toward the base end thereof (toward the finger insertion portion 15) from the distal end side of the slide member 12. Due to this shape of the disengaging movement preventive projection 17d, the slide member 12 and the connecting member 17 that are separate from each other in the axial direction are prevented from moving relative to each other in directions away from each other by the engagement between the disengaging movement preventive recess 12b and the disengaging movement preventive projection 17d. On the other hand, the stepped engaging portion 12a and the stepped engaging portion 17c prevent the slide member 12 and the connecting member 17 from moving relative to each other in directions to approach each other in the axial direction by the engagement of the axially opposed ends of the stepped engaging portion 12a and the stepped engaging portion 17c. In other words, the slide member 12 and the connecting member 17 are connected to each other so as not to move relative to each other in either forward or rearward directions in the axial direction. This connection can be released by radially moving the slide member 12 and the connecting member 17 relative to each other.

As shown in FIG. 6, the outer sheath 11 and the grip portion 14 are provided with two screw holes, respectively, which are aligned in a radial direction, and a slide control screw 22 is screwed into the screw holes therethrough to fix the outer sheath 11 and the grip portion 14 to each other. In addition to the capability of fixing the outer sheath 11 and the grip portion 14 to each other, the slide control screw 22 also serves as a movement limit device which limits the amount of movement of the slide member 12 in the axial direction.

Figure 4:
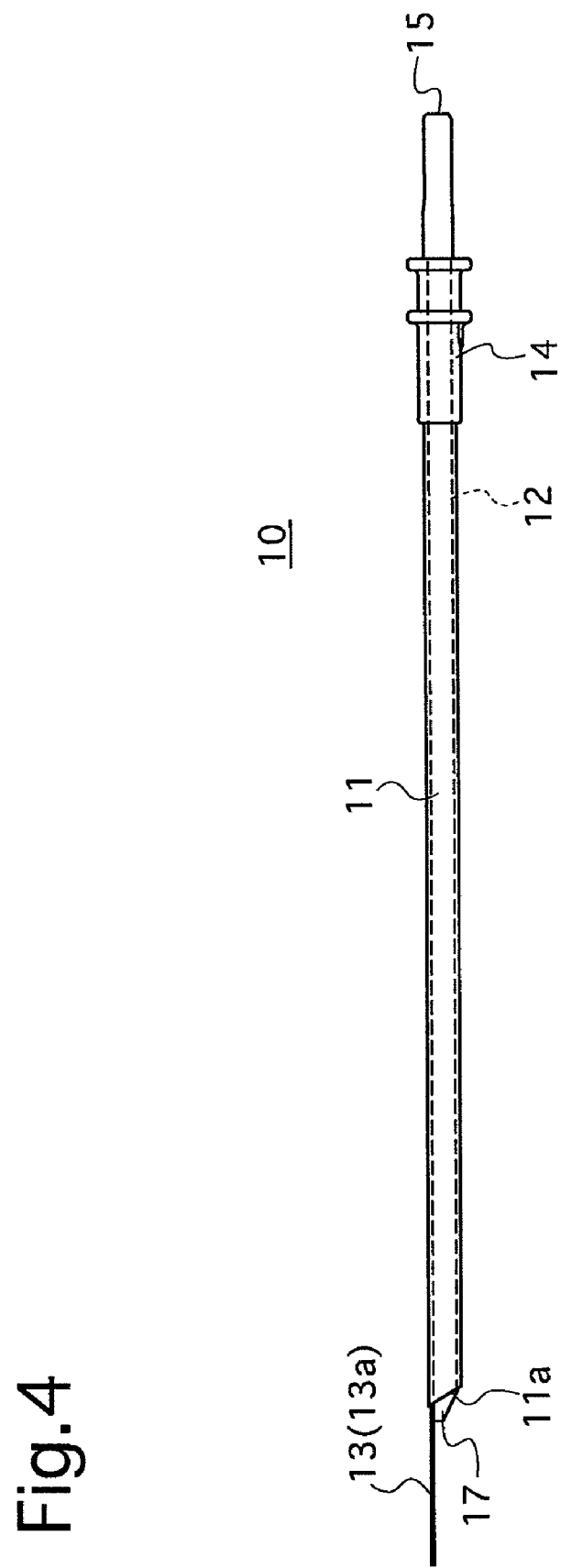
FIG. 4 is a side elevational view of the therapeutic-substance carrying/administering appliance in the state shown in FIG. 1.
Figure 5:
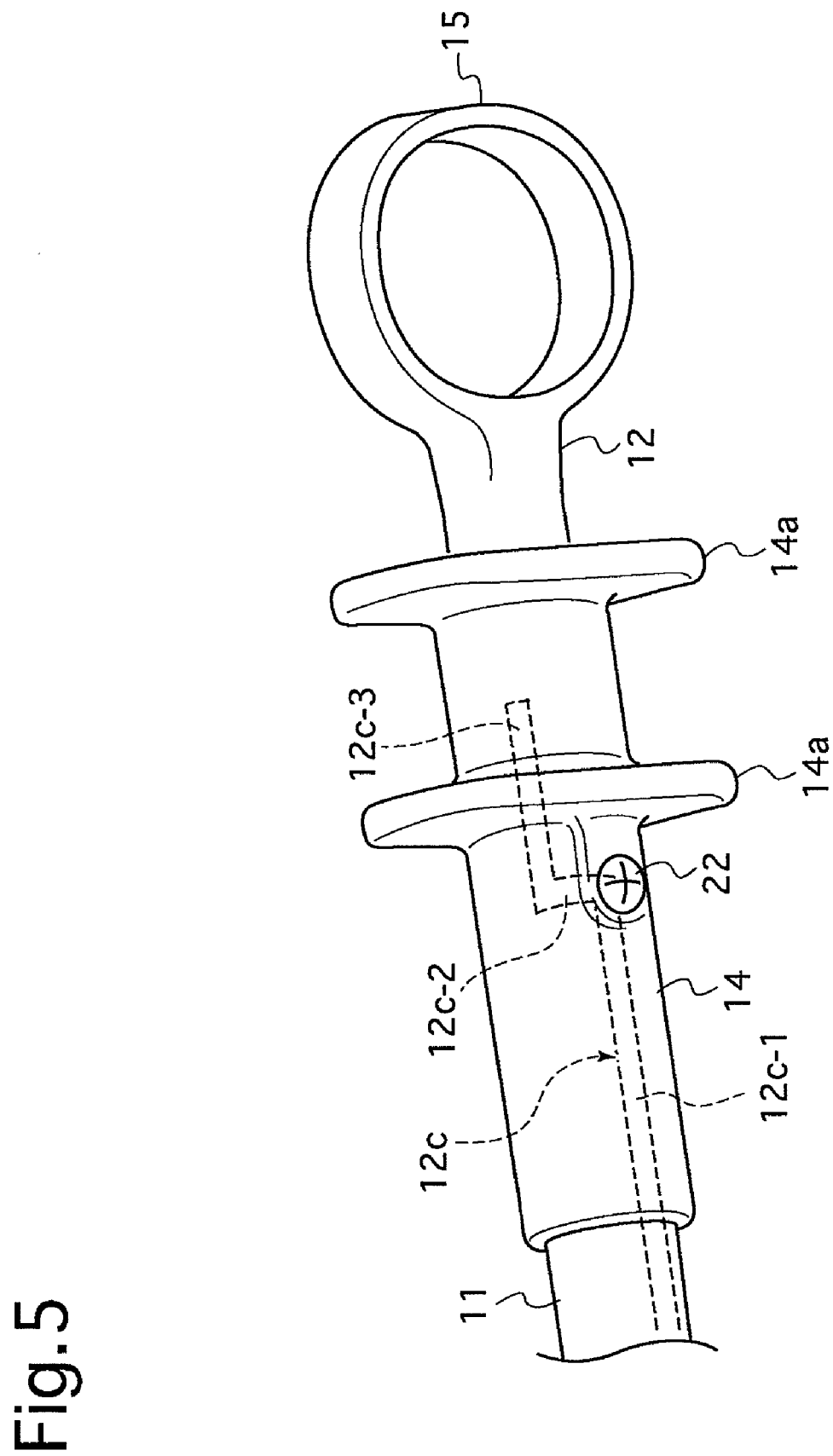
FIG. 5 is a perspective view of a portion of the therapeutic-substance carrying/administering appliance in the vicinity of the hold/control portion thereof.

The end of the slide control screw 22 projects radially inwards from the inner peripheral surface of the outer sheath to be engaged in a limit groove (movement limit device) 12c formed in an outer peripheral surface of the slide member 12. As shown in FIG. 5, the limit groove 12c is formed in a crank shape which includes a first linear groove portion 12c-1, a circumferential groove portion 12c-2 and a second linear groove portion 12c-3, wherein the first linear groove portion 12-1 is elongated in the axial direction of the outer sheath 11, the circumferential groove portion 12c-2 is communicatively connected at its one end to the first linear groove portion 12c-1, and the second linear groove portion 12c-3 is formed to extend from the other end of the circumferential groove portion 12c-2 toward the finger insertion portion 15 in the axial direction of the outer sheath 11. FIG. 6 shows a state where the slide control screw 22 abuts against the terminal of the first linear guide groove portion 12c-1 of the limit groove 12c, i.e., against the circumferential groove portion 12c-2 of the limit groove 12c, which prevents the slide member 12 from further sliding toward the distal end (left end as viewed in FIGS. 3 and 4) of the outer sheath 11 from the position shown in FIG. 6 in the axial direction under normal usage. In this sliding movement limit state of the slide member 12, the junction between the slide member 12 and the connecting member 17 is positioned to be surrounded by the inner peripheral surface of the outer sheath 11 as shown in FIGS. 7 and 8. Although the connecting member 17 is prevented from moving relative to the slide member 12 in the axial direction of the outer sheath 11 (horizontal direction with respect to FIG. 8) and can be disconnected only in a radial direction (vertical direction with respect to FIG. 8) of the outer sheath 11 as noted above, the connecting member 17 and the slide member 12 are prevented from moving relative to each other in this radial direction by the inner peripheral surface of the outer sheath 11 in the state shown in FIG. 8. Namely, the slide member 12 and the connecting member 17 cannot be disconnected from each other under normal usage, in which the slide control screw 22 is positioned in the first linear guide portion 12c-1 of the limit groove 12c.

If the outer sheath 11 and the slide member 12 are rotated relative to each other from the state as shown in FIG. 6, in which the slide control screw 22 abuts against the terminal of the first linear guide groove portion 12c-1 of the limit groove 12c, so that the positions of the second linear guide portion 12c-3 of the limit groove 12c and the slide control screw 22 match with each other in a circumferential direction about the axis of the slide member 12 (the axis of the outer sheath 11), the slide member 12 can further be slid in a direction to project from the distal end of the outer sheath 11 from the position shown in FIGS. 6 through 8. This further sliding movement of the slide member 12 in this direction releases the restriction by the outer sheath 11, thus allowing the connecting member 17 to be removed from the slide member 12. Further removing the slide control screw 22 makes it possible to disengage the slide member 12 and the grip portion 14 from each other.

Although a threads is formed on the entire shaft of the slide control screw 22 shown in FIG. 6, it is possible that no thread be formed on a portion of the shaft of the slide control screw 22 in the vicinity of the end thereof that is engaged with the slide member limit groove 12c. Forming the slide control screw 22 in such a manner to smooth the surface of a portion thereof which comes in sliding contact with the slide member 12 makes it possible to improve the smoothness in sliding operation of the slide member 12.

Figure 3:
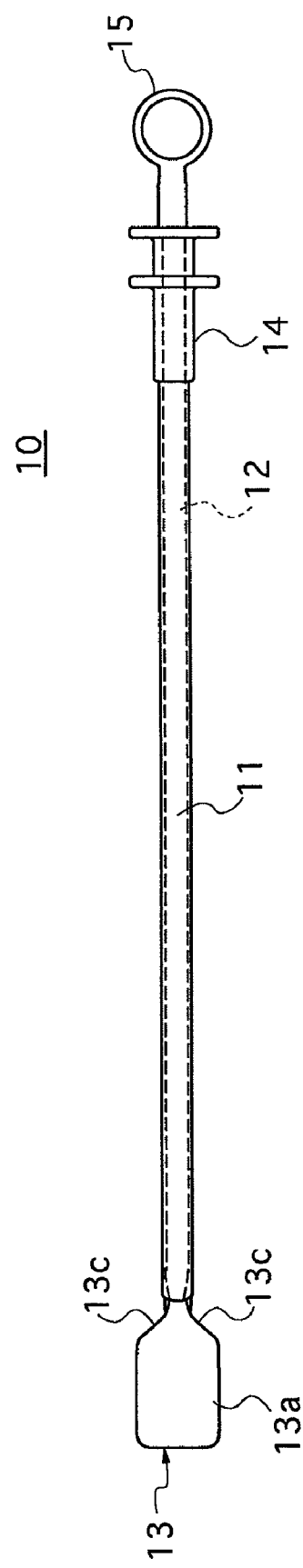
FIG. 3 is a plan view of the therapeutic-substance carrying/administering appliance in the state shown in FIG. 1.
Figure 12:
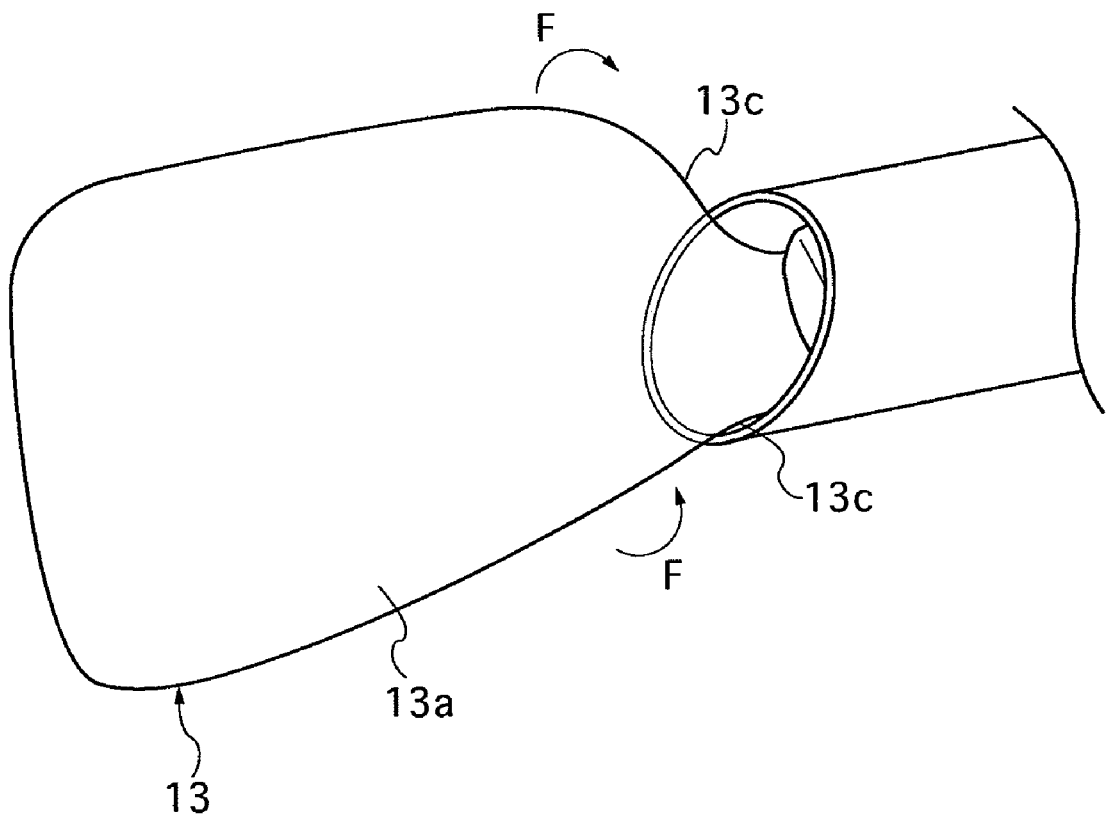
FIG. 12 is a perspective view of the portion of the therapeutic-substance carrying/administering appliance shown in FIG. 11, wherein the sliding member has been slightly retracted into the distal end of the outer sheath from the state shown in FIG. 11, showing a state shortly after the commencement of resilient deformation of the sheet supporting element from the expanded state shown in FIG. 11 to a rolled state shown in FIG. 15.

FIG. 11 shows a state where the slide member 12 is pressed into the outer sheath 11 at the forward movement limit of the slide member 12 relative to the outer sheath 11, which is determined by the above-noted engagement of the slide control screw 22 with the limit groove 12c (the first linear groove portion 12c-1 thereof), under normal usage of the therapeutic-substance carrying/administering appliance 10. In this state, the sheet supporting element 13 projects outwardly from the distal end of the outer sheath 11 and is unrolled so that the sheet-supporting sheet portion 13a is flat by the shape-sustaining ability (resiliency) of the sheet supporting element 13. The width of the sheet supporting element 13 expanded into a flat shape as shown in FIG. 11 is greater than the inner diameter of the outer sheath 11. Sliding the slide member 12 in a retracting direction shown by the arrow S1 shown in FIG. 11 from the state shown in FIG. 11 causes the tapered portion 13c of the sheet supporting element 13 to come in contact with the beveled surface 11a of the outer sheath 11 as shown in FIG. 12. Thereupon, due to the oblique shapes of the beveled surface 11a and the tapered portion 13c, a component force F (see FIG. 12) urging the sheet supporting element 13 to curl into a tubular shape is produced by the sliding movement of the slide member 12 in the axial direction. The inner surface of the sheet supporting element 13 which is about to become tubular in shape at this time serves as a support surface for supporting the sheet 30. Specifically, the surface of the sheet supporting element 13 which appears in FIGS. 11 and 12 is the surface of the sheet supporting element 13 that serves as a support surface for supporting the sheet 30, while the surface of the sheet supporting element 13 which appears in FIGS. 1, 3 and 7 is the undersurface of the sheet supporting element 13, which is positioned on the opposite side of the sheet supporting element 13 from the support surface thereof. In FIGS. 4 and 8, the lower surface of the sheet supporting element 13 is the support surface for supporting the sheet 30, and the upper surface of the sheet supporting element 13 is the undersurface of the sheet supporting element 13, respectively.

Figure 13:
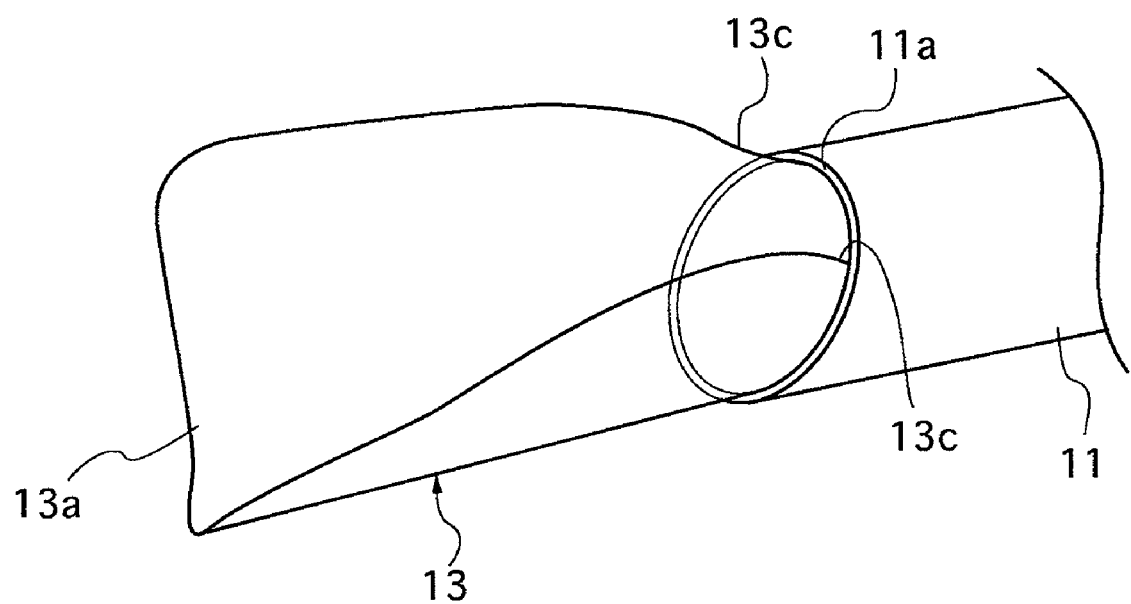
FIG. 13 is a perspective view of the portion of the therapeutic-substance carrying/administering appliance shown in FIG. 11, wherein the sliding member has been slightly retracted further into the distal end of the outer sheath from the state shown in FIG. 12, showing a state where the sheet supporting element has been further deformed from the state shown in FIG. 12 to become closer to the rolled state shown in FIG. 15.
Figure 14:
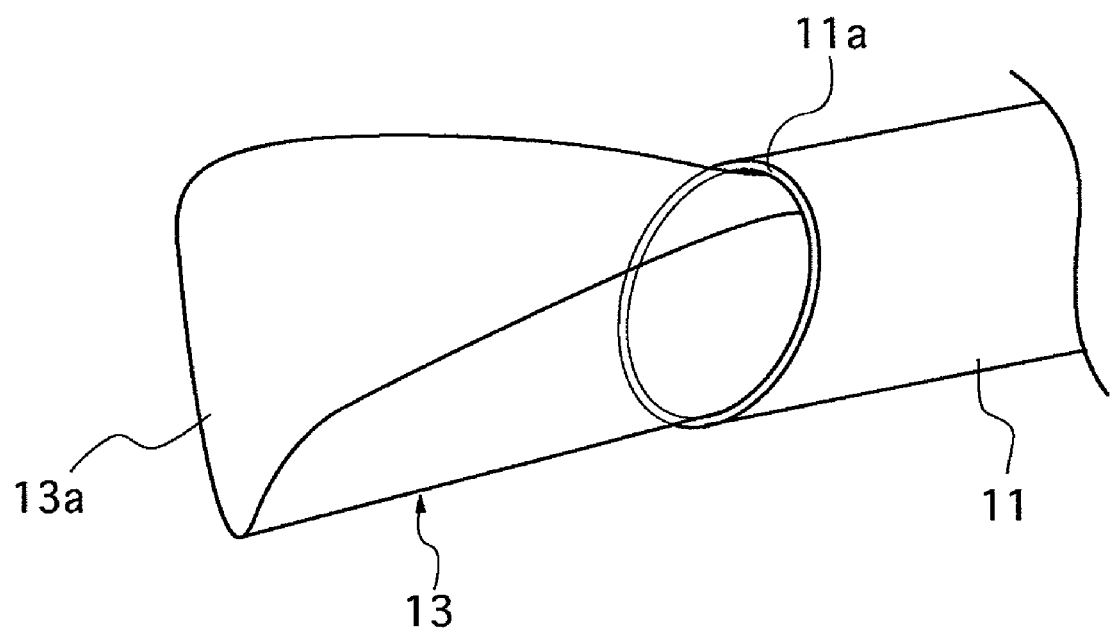
FIG. 14 is a perspective view of the portion of the therapeutic-substance carrying/administering appliance shown in FIG. 11, wherein the sliding member has been slightly retracted further into the distal end of the outer sheath from the state shown in FIG. 13, showing a state where the sheet supporting element has been further deformed from the state shown in FIG. 13 to become closer to the rolled state shown in FIG. 15.

If the slide member 12 continues to be moved in the retracting direction from the state shown in FIG. 12, the sheet supporting element 13 is retracted into the outer sheath 11 to be accommodated therein while being rolled into a tubular shape which is fitted on the inner peripheral surface of the outer sheath 11 in accordance with the retracting movement of the slide member 12 as shown in FIGS. 13 and 14 in that order. At the stage shown in FIG. 13, the tapered portion 13c of the sheet supporting element 13 is still in contact with the beveled surface 11a of the outer sheath 11, and a component force urging the sheet supporting element 13 to curl into a tubular shape acts on the sheet supporting element 13 in accordance with a retracting movement of the slide member 13 in the axial direction. In a state where the sheet supporting element 13 has been retracted to the stage shown in FIG. 14, the tapered portion 13c has been accommodated in the outer sheath 11; however, at the distal end of the outer sheath 11 (the opening of the outer sheath 11 surrounded by the ring-shaped beveled surface 11a), the opposite side edges of the sheet-supporting sheet portion 13a have been brought closer to each other so as to be adjacent to each other, and the sheet-supporting sheet portion 13a has been almost deformed into a substantially tubular shape. Therefore, even if the slide member 12 is slid in the retracting direction from the state shown in FIG. 14, the sheet supporting element 13 moves toward the front end (left end as viewed in FIGS. 3 and 4) of the sheet-supporting sheet portion 13a to retract into the outer sheath 11 while being gradually and smoothly rolled into a tubular shape without being snagged on the beveled surface 11a. Since the outer and inner edges of the beveled surface 11a of the outer sheath 11 are chamfered to eliminate sharp edges, the sheet supporting element 13 is not damaged by coming in sliding contact with the beveled surface 11a during the aforementioned retracting operation of the sheet supporting element 13.

Figure 15:
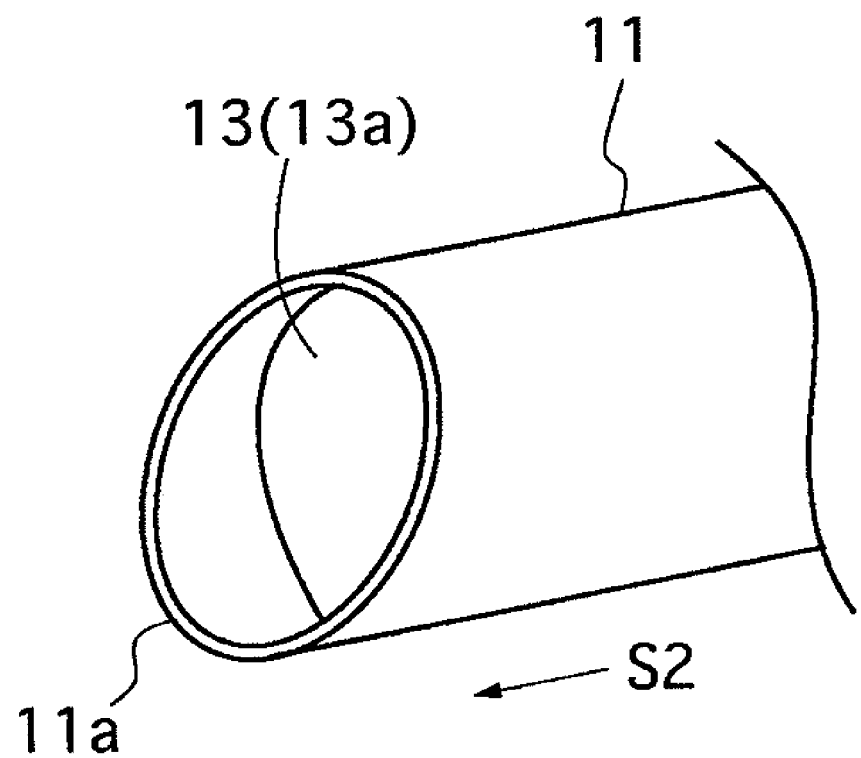
FIG. 15 is a perspective view of the portion of the therapeutic-substance carrying/administering appliance shown in FIG. 11, wherein the sliding member has been fully retracted into the distal end of the outer sheath, showing a state where the sheet supporting element has been rolled into a tubular shape and fully accommodated in the outer sheath.

FIG. 15 shows a state where the sheet supporting element 13 is fully accommodated in the outer sheath 11. In this state, the sheet supporting element 13 has been deformed into a tubular shape fitted on the inner peripheral surface of the outer sheath 11. The width of the sheet supporting element 13 is determined so that the sheet supporting element 13 does not overlap itself in the tubular accommodated state shown in FIG. 15. Specifically, in the case where the inner diameter of the outer sheath 11 is 9.5 mm, the sheet supporting element 13 can be rolled into a tubular shape fitted on the inner peripheral surface of the outer sheath 11 without overlapping itself if the width of the sheet supporting element 13 is approximately 28 mm.

Contrary to the above described case when the slide member 12 is slid in the retracting direction, sliding the slide member 12 in the projecting direction shown by the arrow S2 shown in FIG. 15 from the accommodated state shown in FIG. 15 causes the sheet supporting element 13 to project outwardly from the distal end of the outer sheath 11 while gradually expanding in directions to become flat by the shape-sustaining ability (resiliency) of the sheet supporting element 13, thus causing the shape of the sheet supporting element 13 to change from the deformed state shown in FIG. 15 to the flatter state shown in FIG. 12 via the deformed states shown in FIGS. 14 and 13 in that order. Thereafter, upon the slide member 12 being slid to the maximum projecting position shown in FIG. 11, the tapered portion 13c of the sheet supporting element 13 is disengaged from the beveled surface 11a of the outer sheath 11 to thereby remove restrictions on the shape of the sheet supporting element 13, so that the sheet-supporting plate portion 13a thus having entered a free state expands into a flat shape (original shape).

As shown in FIG. 4, it is desirable that the position of the sheet supporting element 13 in a free state in a radial direction of the outer sheath 11 be decentered from the axis of the outer sheath 11 as much as possible in the direction opposite to the direction of deformation of the sheet supporting element 13 into a tubular shape (i.e., in the upward direction with respect to FIG. 4). Namely, if the sheet supporting element 13 is positioned below the position thereof shown in FIG. 4, e.g., below the axis of the outer sheath 11, the sheet supporting element 13 may get lodged in the outer sheath 11 and thus not be fully accommodated in the outer sheath 11 when the sheet supporting element 13 is attempted to be accommodated in the outer sheath 11 while being deformed into a tubular shape, or the maximum allowable width of the sheet supporting element 13 for accommodation of the sheet supporting element 13 in the outer sheath 11 would be reduced. In contrast, providing the sheet supporting element 13 at a position in close vicinity of the inner edge of the outer sheath 11 in a radial direction (upward direction as viewed in FIG. 4) makes it possible to accommodate the sheet supporting element 13 in the outer sheath 11 smoothly with no interference between the sheet supporting element 13 and the beveled surface 11a, and also makes it possible to increase the aforementioned maximum allowable width of the sheet supporting element 13.

As described above, the sheet supporting element 13 is deformed between a flat unrolled shape and a tubular shape in accordance with advancing/retracting movements of the slide member 12 and has the ability (shape-sustaining ability/resiliency) to unroll naturally into a flat shape upon being brought to project out of the outer sheath 11. For instance, the sheet supporting element 13 having such a shape-sustaining ability can be obtained from a resin film with an appropriate thickness which is made of a material such as polypropylene, acrylic resin, polyethyleneterephthalate or polyethylene. Alternatively, the sheet supporting element 13 having such a shape-sustaining ability can also be obtained from a silicon rubber sheet or a thin metal sheet made of a superelastic alloy or a shape-memory alloy. Additionally, the sheet supporting element 13 can be shaped into a net (wire-net) sheet supporting element instead of the thin-plate-like sheet supporting element 13 as shown in the drawings. Although the flexibility (hardness) of the sheet support member 13 can be freely set by changing the material or thickness thereof, it is desirable that the thickness of the sheet support member 13 be in the order of 50 to 500 micrometers if the sheet support member 13 is made of a resin film such as noted above.

The sheet-supporting sheet portion 13a of the sheet support member 13 is given a surface treatment to be capable of stably supporting the sheet 30. Various surface treatments can be selectively adopted; for instance, the sheet-supporting sheet portion 13a can be coated with a surface material which can be in frictional contact with the sheet 30, or an adhesive layer having a relatively weak adhesive force can be fixed to the surface of the sheet-supporting sheet portion 13a. Specifically, when the sheet 30 is a fibrous therapeutic substance, it is useful to attach a fibrous layer to the sheet-supporting sheet portion 13a. By an intertwist of fibers of the sheet-supporting sheet portion 13a and fibers of the sheet 30, the sheet 30 can be temporarily fixed to the sheet-supporting sheet portion 13a with a certain level of adhesive force preventing the sheet 30 from coming off the sheet-supporting sheet portion 13a when the sheet 30 is carried by the therapeutic-substance carrying/administering appliance 10; moreover, when the sheet 30 is transplanted, the sheet 30 can be easily disengaged from the sheet-supporting sheet portion 13a without being damaged. It is possible to make a cut on a part of the sheet-supporting sheet portion 13a to prevent the sheet 30 from coming off the sheet-supporting sheet portion 13a by physically pinching the part of the sheet-supporting sheet portion 13a. In either case, the sheet-supporting sheet portion 13a is designed to prevent the sheet 30 from coming off the sheet-supporting sheet portion 13a accidentally during carriage of the sheet 30 and to have an appropriate holding force allowing the sheet 30 to come off the sheet-supporting sheet portion 13a to be reliably transplanted to an affected site upon the sheet 30 being transplanted to the affected site. As a configuration for making the sheet 30 come off the sheet-supporting sheet portion 13a easily, for instance, it is possible for micropores to be formed in the sheet-supporting sheet portion 13a beforehand and for physical saline, or the like, to be made to permeate in between the sheet-supporting sheet portion 13a and the sheet 30 through the micropores to form a liquid layer therebetween so that the sheet 30 can be easily peeled off.

As a matter of convenience of the sheet support member 13 when it is used, it is desirable that the sheet supporting element 13 is transparent or translucent. If the sheet supporting element 13 is transparent or translucent, the state of the sheet 30 mounted on the sheet-supporting sheet portion 13a to be supported thereby can be visually checked even from the underside thereof. In addition, during the sheet transplanting operation, one can easily bring the sheet 30 into alignment with an affected site while seeing the position of the affected site through the sheet supporting element 13.

In addition, aside from the capability of holding the sheet 30 and the color setting, various capabilities can be added to the sheet supporting element 13 depending on the usage. For instance, a coating for enhancing the lubricating property of a portion of the sheet supporting element 13 which comes in sliding contact with the outer sheath 11 can be applied to the sheet supporting element 13, or the water repellency of the surface the sheet supporting element 13 can be varied by making selections from various materials and coatings. Additionally, although the sheet-supporting sheet portion 13a of the sheet supporting element 13 in the present embodiment of the therapeutic-substance carrying/administering appliance 10 is substantially rectangular in an unrolled state, the shape of the sheet-supporting sheet portion 13a in an unrolled state is not limited solely to a rectangular shape; the sheet-supporting sheet portion 13a can be formed into any given shape in accordance with the use of the sheet-supporting sheet portion 13a and the shape of the sheet 30.

A manner of using the therapeutic-substance carrying/administering appliance 10 that has the above described structure will be discussed hereinafter. In the present embodiment of the therapeutic-substance carrying/administering appliance 10, a combination of the sheet supporting element 13 and the connecting member 17 constitutes a detachable portion which can be detached from the slide member 12. This detachable portion is replaced by new one after each use. In contrast, a body portion of the therapeutic-substance carrying/administering appliance 10 that consists of the outer sheath 11 and the slide member 12 is made of a material (e.g., a stainless steel) which has sufficient strength and structure capable of resisting repetitive use and sterilization processes. It is possible for this body portion of the therapeutic-substance carrying/administering appliance 10 to be reusable by a sterilization process after use. This reduces the number of disposable parts, which provides better environmental care and also reduces operational cost.

Figure 2:
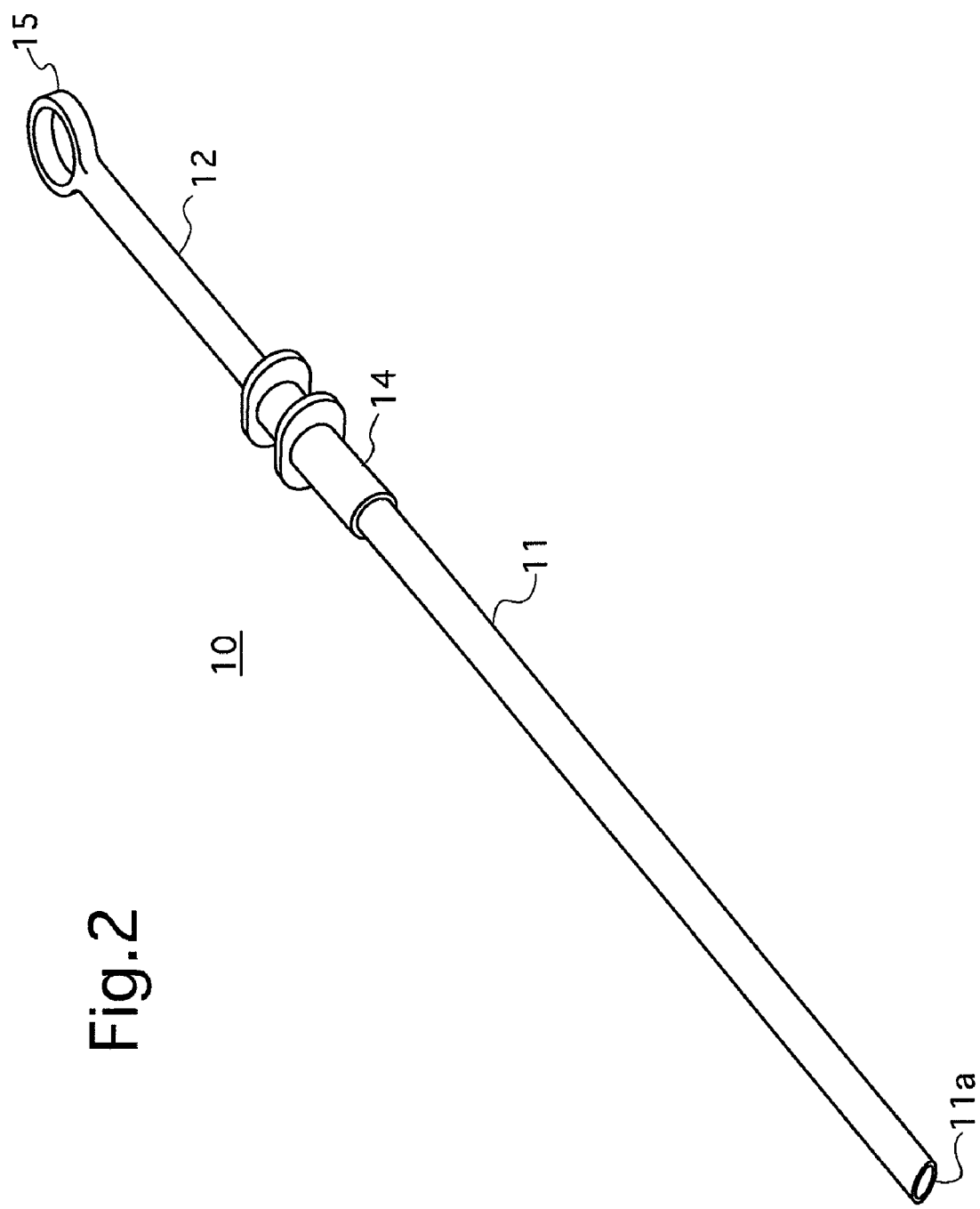
FIG. 2 is a perspective view of the therapeutic-substance carrying/administering appliance shown in FIG. 1 in a state where the sheet supporting element is accommodated in the outer sheath of the appliance.

The detachable portion that includes the sheet supporting element 13 is stabilized and packaged with the sheet 30 being placed on the sheet-supporting sheet portion 13a. When in use, the detachable portion thus packaged is taken out of the package and installed onto the distal end of the slide member 12 via the connecting member 17. At the time of this installation, the slide member 12 is held at a disassembling position at which the slide member 12 is in front of the aforementioned maximum projecting position thereof under normal usage. At this time, the slide control screw 22 is in the second linear groove portion 12c-3 of the limit groove 12c, which serves as a portion thereof for disassembling the therapeutic-substance carrying/administering appliance 10. After the completion of installation of the detachable portion of the sheet supporting element 13 to the distal end of the slide member 12, the slide member 12 is slid in the retracting direction (shown by the arrow S1). This sliding movement of the slide member 12 causes the slide control screw 22 to come in contact with the circumferential groove portion 12c-2 of the limit groove 12c. Thereupon, the slide member 12 is rotated relative to the outer sheath 11 through a predetermined angle of rotation so that the circumferential position of the slide control screw 22 matches with the circumferential position of the first linear groove portion 12c-1 of the limit groove 12c, which is a part of the normal operating range thereof. This state corresponds to the state shown in FIGS. 1, 3, 4, 7 and 11. If the slide member 12 is further slid in the retracting direction, the tapered portion 13c comes in contact with the beveled surface 11a of the outer sheath 11, and subsequently, the sheet supporting element 13 is retracted into the outer sheath 11 to be accommodated therein while being rolled into a tubular shape in the above described manner (from the state shown in FIG. 12 to the state shown in FIG. 15). During this retracting operation of the sheet supporting element 13, the sheet 30 is supported by the inner surface of the sheet-supporting sheet portion 13a having been rolled into a tubular shape, and accordingly, the sheet 30 neither comes in contact with nor rubs against the inner peripheral surface of the outer sheath 11, thus being prevented from being damaged. Upon the sheet supporting element 13 being totally accommodated in the outer sheath 11 as shown in FIG. 2, the sheet 30 is in a state of being protected by the outer sheath 11. Since the sheet supporting element 13 is accommodated in the outer sheath 11 so as not to overlap itself, the sheet 30 supported by the sheet supporting element 13 thereon is also held in a stable shape without being damaged by friction.

Subsequently, the therapeutic-substance carrying/administering appliance 10 is inserted into the body with the sheet supporting element 13 being held in a state where the sheet supporting element 13 is accommodated in the outer sheath 11. More specifically, the outer sheath 11 is inserted into the body via a trockar tube having been inserted into the body when a laparoscopic surgery or thoracoscopic surgery is performed. At this time, the outer sheath 11 can be easily inserted because the distal end of the outer sheath 11 is formed as the beveled surface 11a of the outer sheath 11. The slide member 12 is operated to slide in the projecting direction (shown by the arrow S2) when the distal end of the outer sheath the sheet supporting element 13 and the connecting member 17 is not disengaged from the slide member 12 even if the slide member 12 is moved to the aforementioned maximum projecting 11 reaches a close vicinity of a target transplantation site (affected site) to which the sheet 13 is to be transplanted. Thereupon, the sheet supporting element 13 is projected outwardly from the distal end of the outer sheath 11 and returns to the original shape thereof, so that the sheet-supporting sheet portion 13a expands into a flat shape by the resiliency thereof as shown in FIG. 11. Thereupon, a combination of position of the slide member 12 under normal usage, and accordingly, there is no possibility of the sheet supporting element 13 or the connecting member 17 being accidentally dropped inside the body.

Subsequently, the orientation of the therapeutic-substance carrying/administering appliance 10 is adjusted so that the sheet 30 faces the target transplantation site. Upon the completion of this adjustment, the sheet-supporting sheet portion 13a of the sheet supporting element 13 is brought to be pressed against the target transplantation site. Thereupon, the sheet 30 on the sheet-supporting sheet portion 13a is disengaged from the sheet-supporting sheet portion 13a to be transplanted onto the target transplantation site. As described above, the sheet-supporting sheet portion 13a of the sheet support member 13 is given a surface treatment which prevents the sheet 30 on the sheet-supporting sheet portion 13a from coming off the sheet-supporting sheet portion 13a during carriage of the sheet 30 and which holds the sheet 30 with a certain level of holding force which does not interfere with the transplanting, and the sheet 30 can be detached from the sheet-supporting sheet portion 13a to be reliably transplanted to the target transplantation site by pressing the sheet-supporting sheet portion 13a against the target transplantation site with a predetermined force. Additionally, since the sheet supporting element 13 is flexible, the sheet supporting element 13 can make the shape of the sheet 30 correspond to the shape of a non-flat-shaped target transplantation site also by being flexibly deformed by a certain degree.

The transplanting of the sheet 30 to a target transplantation site can be carried out not only in a manner of simply pressing the sheet-supporting sheet portion 13a against the target transplantation site but also in a different manner. As an example of this different manner, the length of the sheet 30 is preset so that the sheet 30 projects slightly from the front end of the sheet-supporting sheet portion 13a in a state where the sheet 30 is supported by the sheet supporting element 13. With this setting, sliding the sheet supporting element 13 in a plane in which the sheet-supporting sheet portion 13a lies in a direction away from the slightly projecting portion of the sheet 30 (i.e., in a direction toward the connecting portion 13b) while holding this slightly projecting portion with a forceps in a state where the sheet 30 is in contact with the target transplantation site with the sheet supporting element 13 being unrolled causes the sheet 30 to stick to the target transplantation site. Adopting this transplanting manner is effective for the sheet 30 of a particular type which produces water surface tension or adhesion associated with the solubility of the sheet 30 when the sheet 30 touches water.

After the completion of the transplanting of the sheet 30, the sheet supporting element 13 is accommodated in the outer sheath 11 as shown in FIGS. 2 and 15 by sliding the slide member 12 in the retracting direction to pull the therapeutic-substance carrying/administering appliance 10 out of the body. It should be noted that the therapeutic-substance carrying/administering appliance 10 can be pulled out of the body without causing either trouble with a living body or damage to the therapeutic-substance carrying/administering appliance 10 even if the therapeutic-substance carrying/administering appliance 10 is pulled out of the body with the sheet supporting element 13 not yet accommodated in the outer sheath 11 because the trockar tube functions just as with the outer sheath 11 so that the sheet supporting element 13 is deformed into a tubular shape. After the therapeutic-substance carrying/administering appliance 10 is pulled out of the body, the slide member 12 is slid to the aforementioned disassembling position thereof, and thereupon the combination of the sheet supporting element 13 and the connecting member 17 is removed from the slide member 12. If another transplantation (treatment) is required, a new (unused/sterilized) detachable portion with the sheet supporting element 13 is attached to the slide member 12 to perform the subsequent procedure.

As described above, according to the above illustrated embodiment of the therapeutic-substance carrying/administering appliance 10, the degree of invasive medical procedure to a human body can be reduced compared with a technique of carrying the sheet 30 in an unrolled state because the sheet 30 is deformed into a tubular shape and accommodated in the outer sheath 11 and thereafter the sheet 30 is brought to a target transplantation site by making an insertion of the outer sheath 11 into the body. In addition, by pushing the slide member 13 in the projecting direction upon the sheet 30 reaching the target transplantation site, the sheet supporting element 13 automatically unrolls by its shape-sustaining ability (resiliency), and accordingly, the sheet 30 can be transplanted very easily reliably, compared with a conventional method using a forceps or the like. Additionally, since the therapeutic-substance carrying/administering appliance 10 has a simple structure with the flexible sheet supporting element 13 that is deformed between an unrolled state and a tubular housed state in accordance with advancing/retracting movements of the slide member 12, there is little possibility of inconvenience such as a malfunction occurring. Moreover, the cost of production can be minimized since the number of elements of the therapeutic-substance carrying/administering appliance 10 is small and also since individual elements thereof can also be made from low-cost materials.

Figure 16:
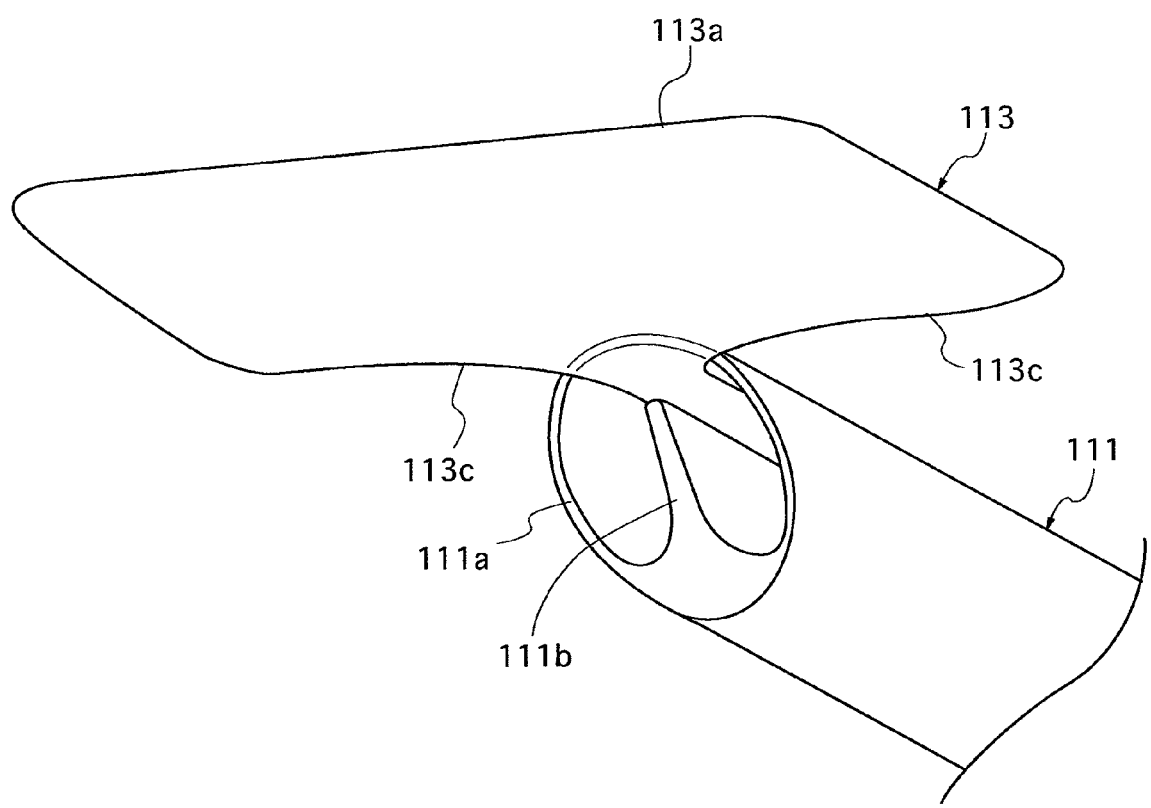
FIG. 16 is a perspective view of another embodiment of the therapeutic-substance carrying/administering appliance according to the present invention, wherein the outer sheath is provided therein with a partition wall which makes it possible to retract a wide sheet supporting element into the outer sheath.
Figure 17:
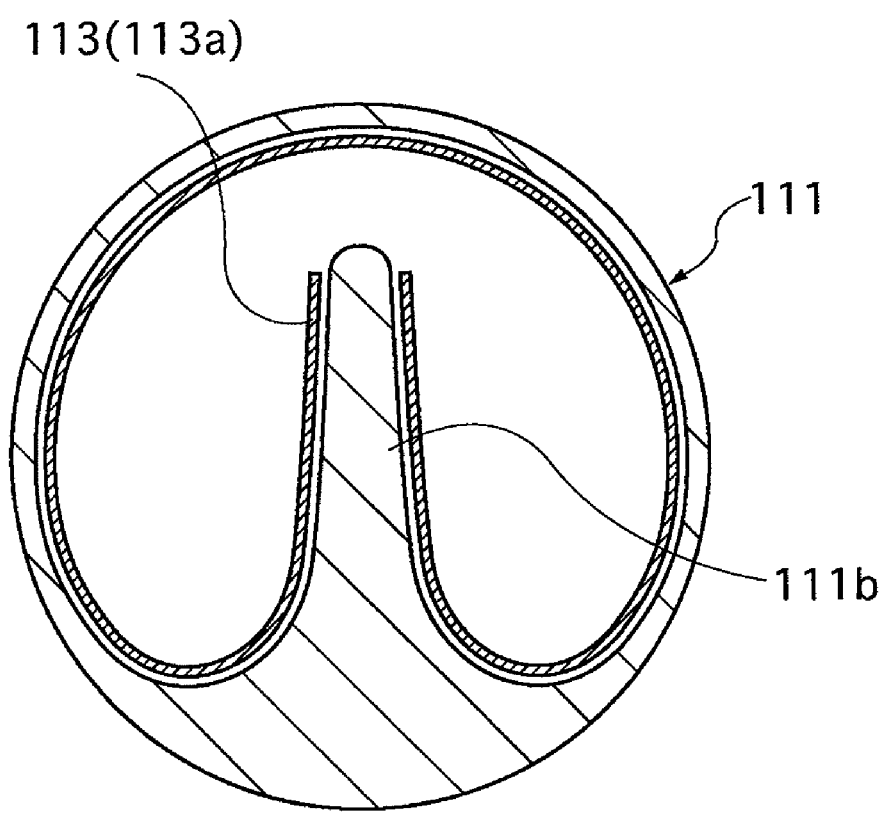
FIG. 17 is a cross sectional view of the therapeutic-substance carrying/administering appliance shown in FIG. 16 in a state where the wide sheet supporting element is retracted into the outer sheath.

FIGS. 16 and 17 show another embodiment (second embodiment) of the therapeutic-substance carrying/administering appliance according to the present invention that can support a wider sheet-shaped therapeutic substance. This embodiment of the therapeutic-substance carrying/administering appliance is provided in an outer sheath 111 with a partition wall 111b which projects radially inwards from an inner peripheral surface of the outer sheath 111. The distal end of the outer sheath 111 is formed as a beveled surface 111a (which corresponds to the beveled surface 11a of the first embodiment of the therapeutic-substance carrying/administering appliance), and a tapered portion 113c (which corresponds to the tapered portion 13c of the first embodiment of the therapeutic-substance carrying/administering appliance) of a sheet supporting element 113 (which corresponds to the sheet supporting element 13 of the first embodiment of the therapeutic-substance carrying/administering appliance) comes in contact with the beveled surface 111a of the outer sheath 111, and subsequently the sheet supporting element 113 is gradually deformed into a tubular shape when the sheet supporting element 113 is retracted into the outer sheath 111 to be accommodated therein. This basic structure of the second embodiment of the therapeutic-substance carrying/administering appliance is the same as that of the first embodiment of the therapeutic-substance carrying/administering appliance. In the first embodiment of the therapeutic-substance carrying/administering appliance, the width size of the sheet-supporting sheet portion 13a is limited to a size smaller than the circumference of the inner periphery of the outer sheath 11 to prevent the sheet supporting element 13 deformed in a tubular shape from overlapping itself in a state where the sheet supporting element 13 is accommodated in the outer sheath 11. In contrast, in the outer sheath 111 of the second embodiment of the therapeutic-substance carrying/administering appliance, providing the outer sheath 111 with the partition wall 111b achieves an increase in the area for supporting the sheet supporting element 113 (inner cross-sectional area of the outer sheath 111), thus making it possible for the outer sheath 111 to accommodate the sheet supporting element 113 that includes the sheet-supporting sheet portion 113a, the width of which is greater than the inner circumference of the outer sheath 111.

Figure 18:
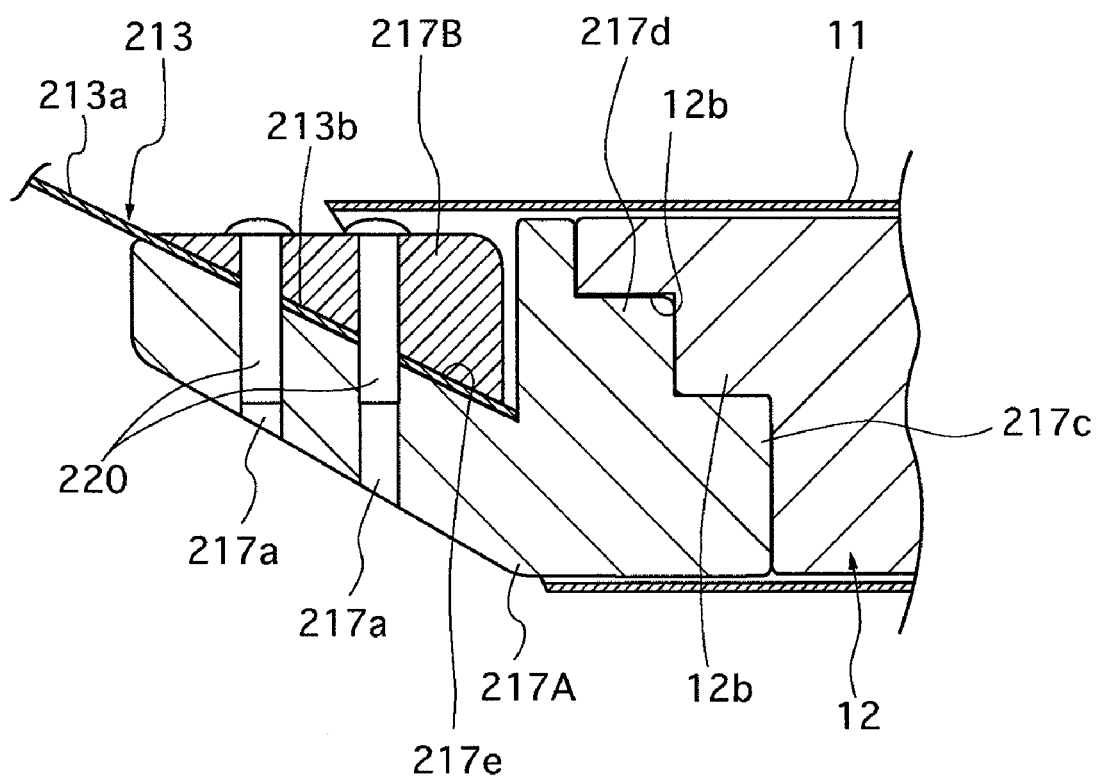
FIG. 18 is a view similar to that of FIG. 8, showing a portion of another embodiment of the therapeutic-substance carrying/administering appliance in the vicinity of the junction between a slide member and a connecting member, wherein the mounting angle of the sheet supporting element relative to the connecting member is different from that shown in FIG. 8.

In addition, although the sheet-supporting sheet portion 13a of the sheet supporting element 13 in an unrolled state is flat, so as to be substantially parallel to the axis of the outer sheath 11 in the first embodiment of the therapeutic-substance carrying/administering appliance, the angle of the sheet supporting element 13 when it is in an unrolled state can be freely determined. FIG. 18 shows an example (third embodiment) of a sheet supporting element having a mounting angle relative to the connecting member that is different from that shown in FIG. 8. A connecting member 217 (which corresponds to the connecting member 17 of the first embodiment of the therapeutic-substance carrying/administering appliance) that can be detached from the slide member 12 via a disengaging movement preventive projection 217d (which corresponds to the disengaging movement preventive projection 17d of the first embodiment of the therapeutic-substance carrying/administering appliance) includes a support block 217A and a pressure block 217B. The support block 217A and the pressure block 217B are fixed to each other by screws 220 which are screwed into screw holes 217a of the connecting member 217, respectively. The support block 217A is provided on the border between the support block 217A and the pressure block 217B with an oblique-flat support surface 217e which is inclined with respect to the axis of the outer sheath 11. A sheet supporting element 213 (which corresponds to the sheet supporting element 13) is held between the support block 217A and the pressure block 217B with a connecting portion 213b (which corresponds to the connecting portion 13b) of the sheet supporting element 213 being mounted on the oblique-flat support surface 217e. Since a sheet-supporting sheet portion 213a (which corresponds to the sheet-supporting sheet portion 13a) of the sheet supporting element 213 lies in a plane in which the oblique-flat support surface 217e lies, the sheet-supporting sheet portion 213a of the sheet supporting element 213 in an unrolled state thereof is given a predetermined angle of inclination relative to the axis of the outer sheath 11 according to the angle of inclination of the oblique-flat support surface 217e.

As described above, in the embodiment (second embodiment) shown in FIGS. 16 and 17, by increasing the inner cross-sectional area of the outer sheath 111 by the formation of the partition wall 111b, the sheet supporting element 113, the width of which is greater than the inner circumference of the outer sheath 111, can be securely accommodated in the outer sheath 111. Unlike this embodiment shown in FIGS. 16 and 17, FIGS. 19 through 21 show another two embodiments of the therapeutic-substance carrying/administering appliances, each of which is configured to make it possible to retract a wide sheet supporting element into the outer sheath smoothly by particular configuration settings on the sheet supporting element.

Figure 19:
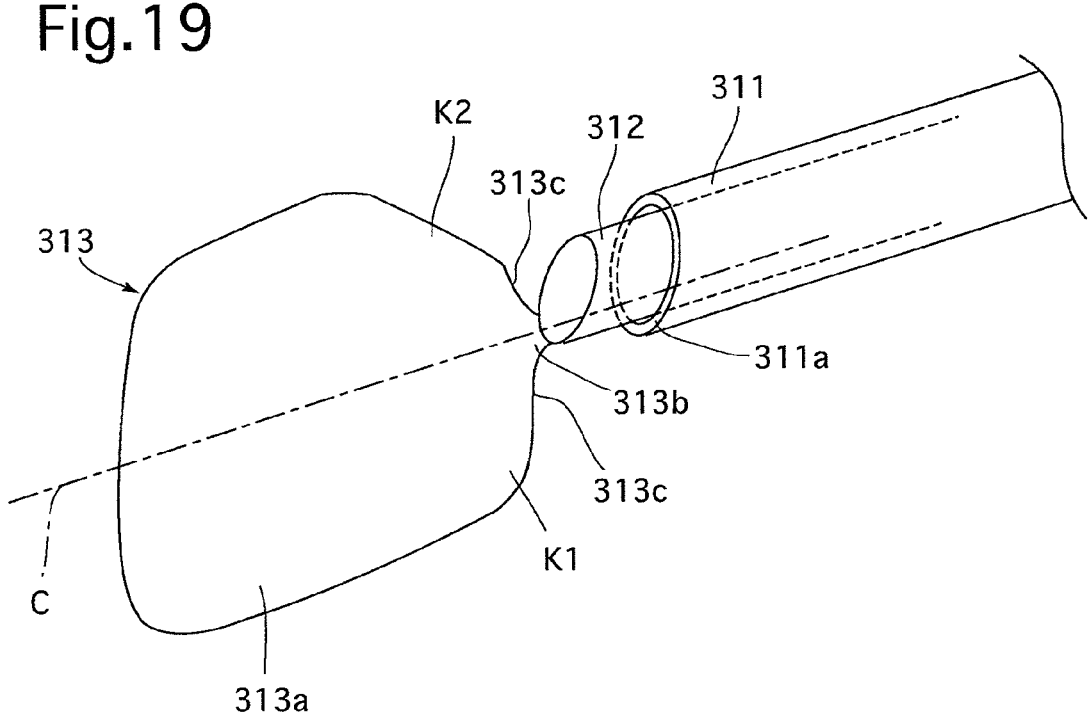
FIG. 19 is a perspective view of a portion of another embodiment of the therapeutic-substance carrying/administering appliance in the vicinity of the distal end of the outer sheath, showing the sheet supporting element in an expanded state, wherein a portion of the sheet supporting element in the vicinity of the fixed end thereof is shaped to be bilaterally asymmetrical.
Figure 20:
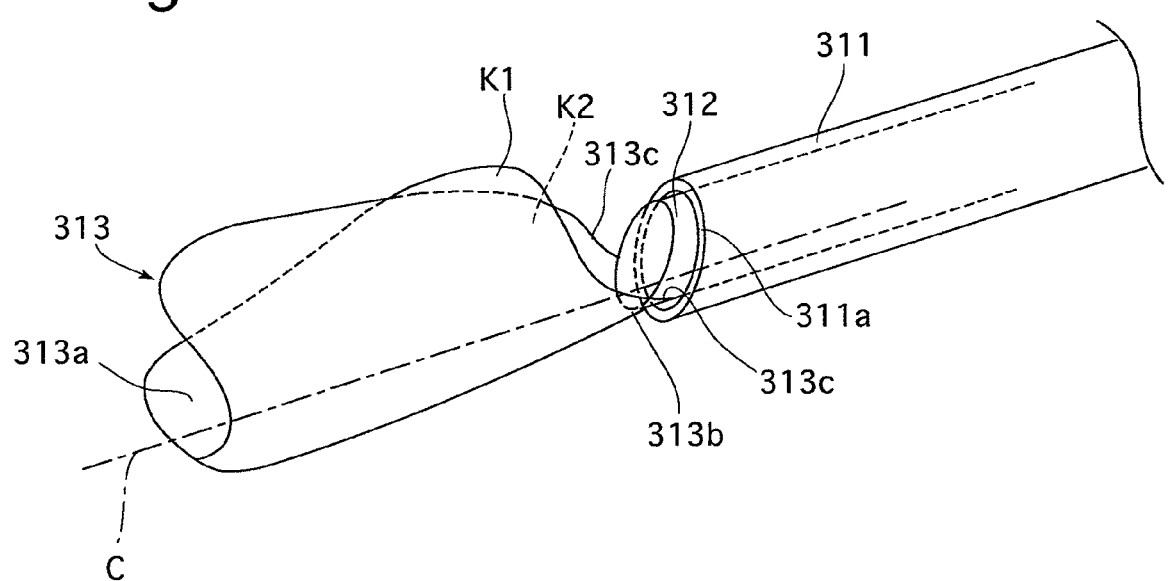
FIG. 20 is a perspective view of the portion of the therapeutic-substance carrying/administering appliance shown in FIG. 19, showing a state where the bilaterally-asymmetrical sheet supporting element is in the process of being deformed into a tubular shape.

A sheet supporting element 313 of the embodiment (fourth embodiment) shown in FIGS. 19 and 20 is supported by the distal end of a slide member 312 (which corresponds to the slide member 12 of the first embodiment of the therapeutic-substance carrying/administering appliance) via a connecting portion 313b, and a tapered portion 313c of the sheet supporting element 313 comes in contact with a beveled surface 311a of the distal end of the outer sheath 311 (which corresponds to the outer sheath 11 of the first embodiment of the therapeutic-substance carrying/administering appliance), and subsequently the sheet supporting element 313 is gradually deformed into a tubular shape when the sheet supporting element 313 is retracted into the outer sheath 311 to be accommodated therein. This basic structure of the embodiment of the therapeutic-substance carrying/administering appliance shown in FIGS. 19 and 20 is the same as that of the first embodiment of the therapeutic-substance carrying/administering appliance.

A feature of the sheet supporting element 313 is that the sheet supporting element 313 includes a portion shaped to be asymmetrical with respect to a central axis C of the sheet supporting element 313 that extends parallel to the axis of the outer sheath 311 and passes through the connecting portion 313b of the sheet supporting element 313. This asymmetrical portion of the sheet supporting element 313 is formed in the vicinity of the fixed end of the sheet supporting element 313 in the area thereof between the tapered portion 313c and a sheet-supporting sheet portion 313a of the sheet supporting element 313. As shown in FIG. 19, the asymmetrical portion of the sheet supporting element 313 includes a normal-shaped portion K1 and a narrowed portion K2 which are positioned on the opposite sides of the central axis C. The narrowed portion K2 is shaped just as the normal-shaped portion K1 with a part thereof cut out.

The width of the sheet supporting element 313 is greater than the circumference of the outer sheath 311, so that the laterally opposite portions of the sheet-supporting sheet portion 313a overlap each other when the sheet supporting element 313 is deformed into a tubular retractable shape. Provided that the sheet supporting element 313 is symmetrical with respect to the central axis C, there is a possibility of the laterally opposite side edges of the sheet-supporting sheet portion 313a interfering with each other and being snagged by each other to thereby hamper the smooth deforming operation of the sheet supporting element 313 when the sheet supporting element 313 is deformed into a tubular shape. In contrast, in the case of the sheet supporting element 313 that is provided in the vicinity of the fixed end thereof with an asymmetrical portion constituted by the normal-shaped portion K1 and the narrowed portion K2, the sheet supporting element 313 is deformed in a manner such that one of the laterally opposite portions thereof on the narrowed portion K2 side reliably slides under (inside) the normal-shaped portion K1 as shown in FIG. 20 when the sheet supporting element 313 is retracted into the outer sheath 311, and therefore, there is no possibility of the laterally opposite edges of the sheet-supporting sheet portion 313a interfering with each other when the sheet supporting element 313 is retracted into the outer sheath 311. Accordingly, the sheet supporting element 313, the width of which is greater than the circumference of the inner peripheral surface of the outer sheath 311, can be smoothly retracted into the outer sheath 311.

Figure 21:
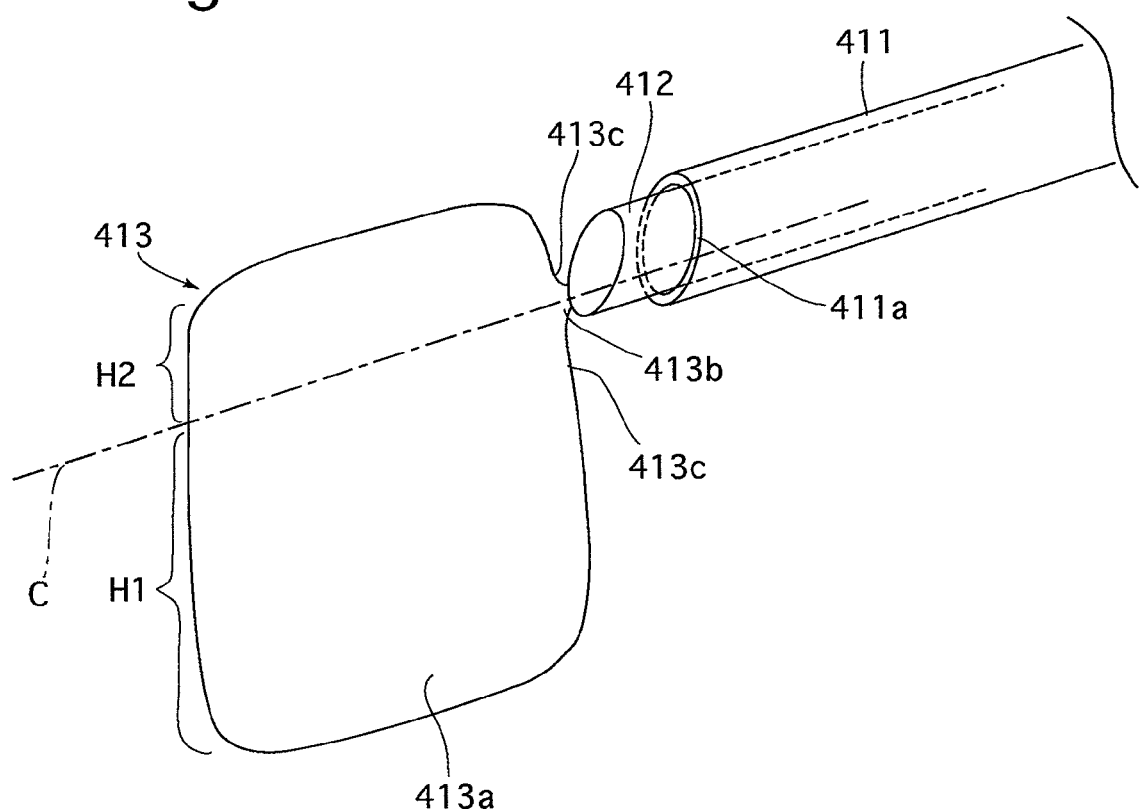
FIG. 21 is a perspective view of a portion of another embodiment of the therapeutic-substance carrying/administering appliance in the vicinity of the distal end of the outer sheath, showing the sheet supporting element in an expanded state, wherein the entire part of the sheet supporting element is shaped to be bilaterally asymmetrical.

Similar to the sheet supporting element 313 in FIGS. 19 and 20, a sheet supporting element 413 of the embodiment (fifth embodiment) shown in FIG. 21 includes a portion shaped to be asymmetrical with respect to a central axis C of the sheet supporting element 413 that extends parallel to the axis of an outer sheath 411 and passes through a connecting portion 413b of the sheet supporting element 413 that is connected to a slide member 412. The sheet supporting element 413 is different from the sheet supporting element 313 of the previous embodiment shown in FIGS. 19 and 20 in that the entire part of the sheet supporting element 413 from the fixed end thereof that is fixed to the slide member 412 to the free end of the sheet supporting element 413 (i.e., from end to end in a direction of the central axis C) is shaped to be bilaterally asymmetrical with respect to the central axis C, whereas only a portion of the sheet supporting element 313 in the vicinity of the fixed end thereof is shaped to be asymmetrical. Namely, the sheet supporting element 413 is shaped to be provided on the opposite sides of the central axis C with a wide portion H1 and a narrow portion H2 having different widths, respectively. In the case of the sheet supporting element 413 having this shape, the sheet supporting element 413 is deformed in a manner such that the narrow portion H2 reliably slides under (inside) the wide portion H1 when the sheet supporting element 413 is retracted into the outer sheath 411 while being rolled into a tubular shape due to the engagement between a beveled surface 411a of the outer sheath 411 and a tapered portion 413c of the sheet supporting element 413, and therefore, there is no possibility of the laterally opposite edges of the sheet-supporting sheet portion 413a interfering with each other when the sheet supporting element 413 is retracted into the outer sheath 411. Accordingly, the sheet supporting element 413, the width of which is greater than the circumference of the inner peripheral surface of the outer sheath 411, can be smoothly retracted into the outer sheath 411.

Although the angles of the pair of side edges of the tapered portion (313c or 413c) relative to the central axis C are substantially identical to each other in each of the sheet supporting element 313 shown in FIGS. 19 and 20 and the sheet supporting element 413 shown in FIG. 21, the sheet supporting element can be shaped to make these angles different from each other to prevent the laterally opposite edges of the sheet supporting element from interfering with each other when the sheet supporting element is retracted into the outer sheath.

Although the present invention has been discussed with reference to the above described embodiments and the accompanied drawings, the present invention is not limited solely to these particular embodiments; making various modifications to the therapeutic-substance carrying/administering appliance is possible without departing from the spirit of the present invention. For instance, although the sliding direction of the slide member 12 and the sliding amount thereof are limited by the engagement between the crank-shaped limit groove 12c and the slide control screw 22 in the above illustrated first embodiment of the therapeutic-substance carrying/administering appliance, an alternative mechanical structure can be adopted as the slide guide structure of the slide member 12.

In the above illustrated first embodiment of the therapeutic-substance carrying/administering appliance, the therapeutic-substance carrying/administering appliance is provided, as a hold/control portion for moving the slide member 12 forward and backward, with the grip portion 14, which includes the pair of finger flanges 14a, and the finger insertion portion 15, whereby the operability similar to that of a syringe is achieved; however, such a hold/control portion can be replaced by a different type of hold/control portion such as a so-called gun-grip type of hold/control portion.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A therapeutic-substance carrying/administering appliance, comprising:
   a cylindrical outer sheath;
   a slide member positioned within said cylindrical outer sheath to be slidable in an axial direction;
   a sheet supporting member connected to a distal end of said slide member and made of a resilient material, said sheet supporting member supporting a sheet-shaped therapeutic substance,
   wherein said sheet supporting member is held in a flat unrolled shape in a free state in which said sheet supporting member projects outwardly from a distal end of said cylindrical outer sheath,
   wherein, when said sheet supporting member is in said free state, sliding said slide member in a retracting direction into said cylindrical outer sheath causes said sheet supporting member to come in contact with said distal end of said cylindrical outer sheath, and subsequently further moving said slide member in said retracting direction causes said sheet supporting member to be retracted into said cylindrical outer sheath while being deformed into a tubular shape, and
   a surface of said sheet supporting member being provided with a surface treatment that supports said sheet-shaped therapeutic substance, wherein said surface treatment comprises an adhesive layer having an adhesive force that temporarily fixes said sheet-shaped therapeutic substance to said sheet supporting member; and
   a connecting member positioned between said sheet supporting member and said slide member,
   wherein a flat support surface of said connecting member contacts a portion of said sheet supporting member.

2. The therapeutic-substance carrying/administering appliance according to claim 1, wherein said sheet supporting member comprises:
   a sheet-supporting sheet portion that defines said surface of said sheet supporting member that is provided with said surface treatment;
   a connecting portion connected to said distal end of said slide member; and
   a tapered portion positioned between said sheet-supporting sheet portion and said connecting portion and shaped so that a width thereof gradually reduces in a direction from said sheet-supporting sheet portion to said connecting portion, wherein, when said sheet supporting member is moved in said retracting direction from said free state, in which said sheet supporting member is held in said flat unrolled shape, said sheet supporting member is deformed into said tubular shape by sliding contact between said tapered portion and said distal end of said cylindrical outer sheath.

3. The therapeutic-substance carrying/administering appliance according to claim 2, wherein said distal end of said cylindrical outer sheath comprises a beveled surface inclined to a plane orthogonal to an axis of said cylindrical outer sheath.

4. The therapeutic-substance carrying/administering appliance according to claim 3, wherein said outer and inner edges of said beveled surface are chamfered.

5. The therapeutic-substance carrying/administering appliance according to claim 1, wherein said sheet supporting member is connectable to and disconnectable from said distal end of said slide member in a radial direction of said cylindrical outer sheath, and wherein said therapeutic-substance carrying/administering appliance further comprises a movement limit device which limits a moving range of said slide member within a range in which an inner peripheral surface of said cylindrical outer sheath prevents said sheet supporting member from being disconnected from said distal end of said slide member.

6. The therapeutic-substance carrying/administering appliance according to claim 5, wherein said movement limit device comprises:

a groove formed on said slide member, and a screw screwed into said cylindrical outer sheath to be engaged in said groove.

7. The therapeutic-substance carrying/administering appliance according to claim 1, wherein said cylindrical outer sheath comprises a partition wall positioned inside said cylindrical outer sheath to increase an inner peripheral area of said cylindrical outer sheath.

8. The therapeutic-substance carrying/administering appliance according to claim 7, wherein said partition wall projects radially inwards from said inner peripheral surface of said cylindrical outer sheath to a position so that internal spaces of said cylindrical outer sheath on opposite sides of said partition wall are communicatively connected to each other.

9. The therapeutic-substance carrying/administering appliance according to claim 1, wherein said sheet supporting member, in said free state, is supported by said flat support surface of said connecting member such that said sheet supporting member is oriented flat and substantially parallel to an axis of said cylindrical outer sheath.

10. The therapeutic-substance carrying/administering appliance according to claim 1, wherein said flat support surface of said connecting member is an oblique flat support surface, and wherein said sheet supporting member, in said free state, is supported by said oblique flat support surface of said connecting member such that said sheet supporting member is oriented flat and inclined to an axis of said cylindrical outer sheath.

11. The therapeutic-substance carrying/administering appliance according to claim 1, wherein said sheet supporting member in said free state comprises a portion shaped to be asymmetrical with respect to a central axis of said sheet supporting member, wherein said central axis is parallel to an axis of said cylindrical outer sheath and passes through a connecting portion of said sheet supporting member which is connected to said distal end of said slide member.

12. The therapeutic-substance carrying/administering appliance according to claim 11, wherein said asymmetrical-shaped portion of said sheet supporting member is formed in a vicinity of said connecting portion.

13. The therapeutic-substance carrying/administering appliance according to claim 11, wherein an entire part of said sheet supporting member, from opposite ends in a direction of said central axis, is shaped to be bilaterally asymmetrical with respect to said central axis.

14. A therapeutic-substance carrying/administering appliance comprising:

a cylindrical outer sheath;

a slide rod inserted in said cylindrical outer sheath to be slidable relative to said cylindrical outer sheath; and a resilient sheet fixed to a distal end of said slide rod, a sheet-shaped therapeutic substance being mountable on said resilient sheet, wherein said resilient sheet is flat in a free state in which said resilient sheet projects outwardly from said distal end of said cylindrical outer sheath, and wherein sliding said slide rod in a retracting direction into said cylindrical outer sheath causes laterally opposite edges of said resilient sheet in a vicinity of said distal end of said slide rod to slide on said distal end of said cylindrical outer sheath while said resilient sheet is deformed into a tubular shape to be retracted into said cylindrical outer sheath, and a surface of said resilient sheet being provided with a surface treatment that supports said sheet-shaped therapeutic substance, wherein said surface treatment comprises an adhesive layer having an adhesive force that temporarily fixes said sheet-shaped therapeutic substance to said resilient sheet; and a connecting member positioned between said sheet supporting member and said slide member, wherein a flat support surface of said connecting member contacts a portion of said sheet supporting member.

* * * * *